United States Patent
Mitarai et al.

(10) Patent No.: US 9,828,612 B2
(45) Date of Patent: Nov. 28, 2017

(54) METHOD FOR PRODUCING ALCOHOL USING TREE AS STARTING MATERIAL AND ALCOHOL SOLUTION OBTAINED BY SAME

(75) Inventors: Kaoru Mitarai, Saiki (JP); Miho Sakai, Oita (JP); Kenji Matsui, Yao (JP)

(73) Assignees: Meisho Co., Ltd., Saiki-Shi (JP); Fujisawa Environment Development Co., Ltd., Oita-Shi (JP)

( * ) Notice: Subject to any disclaimer, the term of this patent is extended or adjusted under 35 U.S.C. 154(b) by 989 days.

(21) Appl. No.: 14/119,320

(22) PCT Filed: May 23, 2012

(86) PCT No.: PCT/JP2012/063224
§ 371 (c)(1),
(2), (4) Date: May 22, 2014

(87) PCT Pub. No.: WO2012/161230
PCT Pub. Date: Nov. 29, 2012

(65) Prior Publication Data
US 2014/0373582 A1    Dec. 25, 2014

Related U.S. Application Data

(60) Provisional application No. 61/489,011, filed on May 23, 2011, provisional application No. 61/528,973, filed on Aug. 30, 2011.

(51) Int. Cl.
| | |
|---|---|
| *C12P 1/00* | (2006.01) |
| *C12N 9/00* | (2006.01) |
| *C12P 7/02* | (2006.01) |
| *C12P 7/10* | (2006.01) |
| *C12P 39/00* | (2006.01) |
| *C12P 7/14* | (2006.01) |
| *C05F 11/00* | (2006.01) |
| *C12F 3/10* | (2006.01) |
| *C12G 3/02* | (2006.01) |
| *A23K 10/38* | (2016.01) |

(52) U.S. Cl.
CPC .............. *C12P 7/02* (2013.01); *A23K 10/38* (2016.05); *C05F 11/00* (2013.01); *C12F 3/10* (2013.01); *C12G 3/02* (2013.01); *C12P 7/10* (2013.01); *C12P 7/14* (2013.01); *C12P 39/00* (2013.01); *C12P 2203/00* (2013.01); *Y02E 50/16* (2013.01); *Y02E 50/17* (2013.01)

(58) Field of Classification Search
CPC ..................................... C12P 1/00; C12N 9/00
See application file for complete search history.

(56) References Cited

U.S. PATENT DOCUMENTS 5,520,933 A * 5/1996 Yoshida .................. A23L 27/24
426/11

FOREIGN PATENT DOCUMENTS

| JP | 2004-141141 A | 5/2004 |
| JP | 2006-131487 A | 5/2006 |
| JP | 2006-180832 A | 7/2006 |
| JP | 4113252 B2 | 4/2008 |
| JP | 2010-259392 A | 11/2010 |

OTHER PUBLICATIONS

Office Action issued by IP Australia (Patent Office) for Australia Patent Application No. 2012259880 dated Jun. 10, 2015.
International Search Report (PCT/JP2012/063224).

\* cited by examiner

*Primary Examiner* — Scott Long
*Assistant Examiner* — Natalie Moss
(74) *Attorney, Agent, or Firm* — Baker & Hostetler LLP

(57) ABSTRACT

A method is provided for the production of alcohol from trees, the method comprising a step of treating a subject tree with mother cell lyases formed through cytolysis associated with sporulation of spore-forming aerobic bacteria, thereby degrading said tree into a powdery state and obtaining a tree degradation product; a step of sterilizing said tree degradation product; a step of treating said sterilized tree degradation product with a koji fungus (*Aspergillus oryzae*) thereby carrying out a primary fermentation; a step of adding a yeast to the fermentation broth obtained by said primary fermentation thereby carrying out a secondary fermentation; and a step of filtering the fermentation broth obtained by said secondary fermentation, wherein said mother cell lyases are obtained by culturing said spore-forming aerobic bacteria, subjecting the resultant culture medium to a starvation state, thereby converting said bacteria into endospores, and removing impurities including said endosporic bacteria from said culture medium and wherein said spore-forming aerobic bacteria are MRE symbiotic bacteria.

5 Claims, 28 Drawing Sheets

Flow for Alcohol Fermentation after Saccharification Using Amazake Koji Fungus

FIG. 3A — Flow for Mycelial Growth Test by Koji Fungus Type

FIG. 3B — Flow for Mycelial Growth Test by % Hydration

Flow for Alcoholic Fermentability Study Experiment, by Yeast

Flow for Stage Feeding of MRE-treated Bamboo Alone

Stage Feeding of MRE-treated Bamboo with Uniformly Mixed Rice Koji Fungus

Stage Feeding of MRE-treated Bamboo with Step-by-step Decremental Rice Koji Fungus

Stage Feeding of MRE-treated Bamboo with Step-by-step Incremental Rice Koji Fungus

Flow Sheet for Large Volume Fermentation Experiment for MRE-treated Bamboo

Alcoholic Fermentability Study, by Yeast (First Study)

Glucose Concentration by Yeast for Day 0 and Day 3 (First Study)

|  | Control | Baker's Yeast | S.celevisiae NBRC0244 | S.celevisiae NBRC0249 | S.celevisiae NBRC2373 |
|---|---|---|---|---|---|
| 0 time | 0.018 | 0.018 | 0.018 | 0.018 | 0.018 |
| 1day | 0.009 | 0.050 | 0.037 | 0.033 | 0.034 |
| 2days | 0.010 | 0.051 | 0.038 | 0.031 | 0.038 |
| 3days | 0.008 | 0.053 | 0.036 | 0.030 | 0.034 |

Alcoholic Fermentability Study, by Yeast (Second Study)

|  | Control | Baker's Yeast | S.celevisiae NBRC0244 | S.celevisiae NBRC0249 | S.celevisiae NBRC2373 |
|---|---|---|---|---|---|
| 0 time | 0.12 | 0.12 | 0.12 | 0.12 | 0.12 |
| 1day | 0.12 | 0.05 | 0.04 | 0.050 | 0.04 |
| 2days | 0.13 | 0.03 | 0.04 | 0.120 | 0.02 |
| 3days | 0.1 | 0.04 | 0.03 | 0.100 | 0.04 |

Unite (g/L)

Glucose Assimilation Study, by Yeast (Second Study)

9 Day Alcoholic Fermentation with Stage Feeding of MRE-treated Bamboo and Glucose Concentration (Before Distillation)

9 Day Alcohol Concentration with Stage Feeding of MRE-treated Bamboo Along with Rice Koji Fungus Uniformly Mixed Therein and Glucose Concentration (Before Distillation)

9 Day Alcohol Concentration of Stage Feeding of MRE-treated Bamboo with Step-by-step Decremental Rice Koji Fungus Thereto and Glucose Concentration (Before Distillation)

9 Day Alcohol Concentration of Stage Feeding of MRE-treated Bamboo with Step-by-step Incremental Rice Koji Fungus Thereto and Glucose Concentration (Before Distillation)

Graphs Comparing Alcohol Concentration of Distillate Fractions for Bamboo Shochu Liquor with Rice Koji Fungus Fed Thereto

Results of Large Volume Alcoholic Fermentation

Alcoholic Fermentation Flow Sheet Using MRE-treated Sugi Cedar or Hinoki Cypress

𝓕𝐼𝒢. 23

Alcoholic Fermentability Study Experiment Flow, by Yeast

Alcoholic Fermentation Flow for Stage Feeding of MRE-treated Sugi Cedar or Hinoki Cypress

Glucose Assimilation Study with MRE-treated Sugi Cedar, by Yeast

Alcoholic Fermentability Study with MRE-treated Hinoki Cypress, by Yeast

Glucose Assimilation Study with MRE-treated Hinoki Cypress, by Yeast

9 Day Alcoholic Fermentation with Stage Feeding of MRE-treated Sugi Cedar alone and Glucose Concentration (Before Distillation)

9 Day Alcoholic Fermentation with Stage Feeding of MRE-treated Hinoki Cypress alone and Glucose Concentration (Before Distillation)

Method for Production of MRE-treated Bamboo

METHOD FOR PRODUCING ALCOHOL USING TREE AS STARTING MATERIAL AND ALCOHOL SOLUTION OBTAINED BY SAME

CROSS REFERENCE TO RELATED APPLICATIONS

This application is a United States national phase of co-pending international patent application No. PCT/JP2012/063224, filed May 23, 2012, which claims benefit of U.S. provisional application No. 61/489,011, filed May 23, 2011 and U.S. provisional application No. 61/528,973, filed Aug. 30, 2011, the disclosures of which are incorporated herein by reference.

FIELD OF THE INVENTION

The present invention relates to a method for producing alcohol from trees and an alcohol solution thereby obtained. Specifically, the present invention relates to a method for producing alcohol by fermenting trees which are intrinsically difficult to ferment.

BACKGROUND OF THE INVENTION

Currently, approaches are being made worldwide, targeted at a low-carbon society against a backdrop of global warming and crude oil depletion problems. Among such efforts, attention is being focused on energy production methods utilizing biomass; in particular it is bioethanol as an energy alternative to gasoline that is gaining a spotlight. However, because the production of bioethanol uses as a feedstock starch and carbohydrates which are used as food, their conversion to bioethanol production is considered limited from standpoints such as a rise in grain prices and the food crises.

This has led to studies of methods for producing ethanol using wood-based biomass feedstock which does not compete with food, whereby cellulose is subjected to a chemical treatment and use of microorganism's enzymes, and like. However, there also exists a substantial obstacle of production costs in the production of alcohol for fuel using the wood-based biomass, making it currently difficult to use it as for-fuel alcohol.

On another front, studies have been ongoing to utilize wood-based biomass for food supply. For example, Patent Reference 1 is for producing a fertilizer by fermenting the sheaths of bamboo shoot or young bamboo and Patent Reference 2 for producing a health food ingredient containing theanine and the like. However, Patent Reference 1 is exclusively for producing a fertilizer, and not possible to make food. Further, Patent Reference 2 uses anaerobic bacteria making it unfit for seasonings and beverages.

Patent Reference 3 proposes a method for producing bamboo vinegar as a health food free from carcinogens such as benzpyrene or substances hazardous to the human body, which are found in a bamboo vinegar obtained from distillation of smoke that accompanies the conventional bamboo charcoal production. However, the distillation thereof at low temperature under reduced pressure ends up taking as long as 5 to 15 days and the product contains many impurities. Further, Patent Reference 4 proposes a method of an alcoholic fermentation using koji fungus (*Aspergillus oryz*) but it uses grain as feedstock so that the same procedure without change cannot be adapted for production of a fermentation product of trees such as bamboo containing antimicrobials.

PRIOR ART DOCUMENTS

Patent References

[Patent Reference 1] Japanese Laid-Open Patent Publication No. 2006-131487
[Patent Reference 2] Japanese Laid-Open Patent Publication No. 2006-180832
[Patent Reference 3] Japanese Laid-Open Patent Publication No. 2004-141141
[Patent Reference 4] Japanese Patent No. 4113252

SUMMARY OF THE INVENTION

The present invention, made in view of such situations as the above, aims to ferment trees, which are difficult to ferment because they contain a characteristic antimicrobial substance, and to produce alcohol usable as for-fuel alcohol or as food. It further aims to provide safe alcoholic beverages and alcohol-containing foods, by not performing any chemical treatment with chemicals such as sulfuric acid, but by brewing a beverage alcohol using bacteria originally present in the natural world.

Furthermore, the present invention aims to make an effective use of fermentation residues, which require waste disposal, not insubstantial in the conventional production of alcoholic fermentation beverages, by not performing a chemical treatment or genetically modifying the bacteria, thereby allowing the use of fermentation residues and/or post-fermentation broth or the like that are discharged after an alcoholic fermentation, as livestock feed or as a plant fertilizer.

The present invention is based on the observation that koji fungus or yeast is capable of an alcoholic fermentation, directly from a tree degradation product, of only the cellulose and/or carbohydrates in the tree itself, without feeding carbohydrates such as grain or bran. The present inventors discovered that the treating of trees that had been difficult to ferment with koji fungus or yeast, because they contain their characteristic antimicrobials and are essentially devoid of any nutrients making it difficult for the koji fungus or yeast to survive and propagate, with mother cell lyases according to the present invention, enable them, as a feedstock, to be fermented by said koji fungus or yeast.

Therefore, according to a first principal aspect of the present invention, a method is provided for producing alcohol from trees, the method comprising a step of applying mother cell lytic enzymes formed through cytolysis associated with a spore formation of a spore-forming aerobic bacteria to a tree, thereby degrading the tree into a powdery state and obtaining a tree degradation product; a step of sterilizing the tree degradation product; a step of applying a koji fungus (*Aspergillus oryzae*) to the sterilized tree degradation product thereby carrying out a primary fermentation; a step of adding a yeast to a fermentation broth obtained by the primary fermentation thereby carrying out a secondary fermentation; and a step of filtering a fermentation broth obtained by the secondary fermentation, wherein the mother cell lytic enzymes are obtained by incubating the spore-forming aerobic bacteria, placing a resultant culture medium under a starvation condition, thereby causing the bacteria to internally sporulate, and removing from a culture medium impurities containing the internally sporulated bacteria, and wherein the spore-forming aerobic bacteria is an MRE symbiotic bacteria group.

Such constitution as described can provide a method of performing an alcoholic fermentation by koji fungus or yeast, directly from a tree degradation product, of only the cellulose and/or carbohydrates in the tree itself, without feeding carbohydrates such as grain or bran. Further, according to the present invention, the tree degradation product, which is the alcohol-feedstock, is merely sterilized, so that it can provide alcohol retaining the components intrinsic in the tree as well as the flavor of the tree.

According to an embodiment of the present invention, in such a method, the tree is selected from bamboo, Japanese cedar (sugi cedar. *Cryptomeria japonica*), and Japanese cypress (hinoki cypress, *Chamaecyparis obtusa*).

In addition, according to another embodiment of the present invention, in such a method, the koji fungus in the method is selected from *Aspergillus amazake, Aspergillus orgzae* (NBRC30104), *Aspergillus orgzae* (NBRC30113), *Aspergillus cellulosae* (NBRC4040), *Aspergillus cellulosae* (IFO4297), *Aspergillus usami* (NBRC4033), and *Aspergillus awamori* (NBRC4388).

In addition, according to yet another embodiment of the present invention, in such a method, the yeast is selected from bakers' yeasts, *Saccharomyces celevisiae* (NBRC0244), *Saccharomyces celevisiae* (NBRC0249). *Saccharomyces celevisiae* (NBRC0282), *Saccharomyces celevisiae* (NBRC2373). *Saccharomyces celevisiae* (NBRC2377), and *Saccharomyces celevisiae* (IFO1728).

According to yet another embodiment of the present invention, in the method, the tree is immersed in a degradation solution containing the mother cell lytic enzymes and/or spores formed by spore formation of the spore-forming aerobic bacteria, and is degraded by aerating the solution.

According to a second principal aspect of the present invention, distilled spirit (shochu liquor) is provided that contains alcohol solution obtained by the above-mentioned method.

Furthermore, according to a third principal aspect of the present invention, a fermentation residue is provided that is obtained in a production process of alcohol solution produced by the method described above, wherein the fermentation residue is obtained by filtering the fermentation broth produced by the secondary fermentation.

According to one embodiment of the present invention, in such a fermentation residue, the fermentation residue is used as an agricultural compost or livestock feed.

Additionally, the characteristics and significant features and effects other than those described above will be apparent to those skilled in the art by referring to the following embodiment sections and drawings of the invention.

DETAILED DESCRIPTION OF THE INVENTION

Figures 1A, 1B:
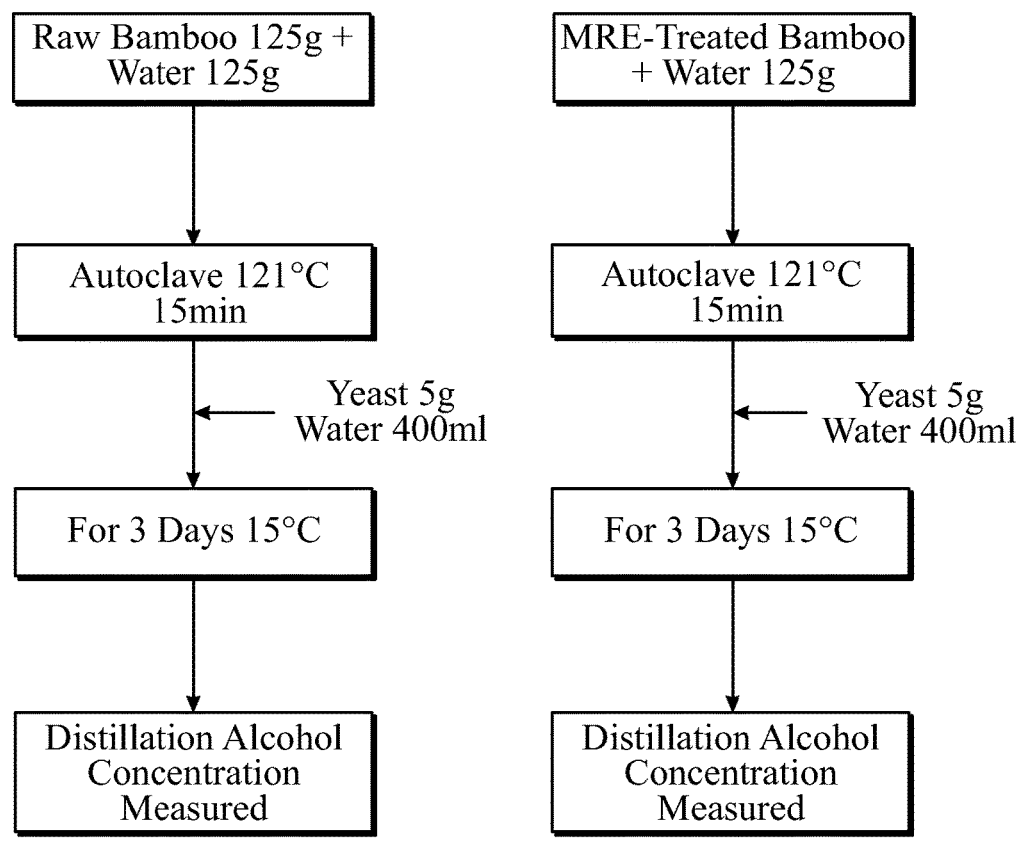
FIG. 1 is a flow sheet for an alcoholic fermentation in one embodiment of the present invention.

As described above, the present invention provides a method for producing alcohol by degrading trees using mother cell lyases released during cytolysis associated with sporulation of aerobic spore-forming bacteria, causing said tree as a feedstock to be fermented with a designated koji fungus thereby forming a primary fermentation broth containing ethanol and/or umami (savory taste) components, and further carrying out a secondary fermentation to elevate the ethanol concentration using a designated yeast. In addition, the aerobic spore-forming bacteria are not particularly limited as long as they form endospores, and are preferably MRE symbiotic bacteria. Furthermore, the aerobic bacteria used in the method of the present invention may be mixed bacteria comprising one or more aerobic bacteria.

Trees such as bamboo and the like have heretofore never been fermented for use in beverages or food. This is because antimicrobial substances present therein such as 2,6-dimethoxy 1,4 benzoquinone, p-benzoquinone, and tannins hinder the activity of koji fungus and the like, making it difficult to sustain fermentation with koji fungus or yeast. Further, the production of alcohol using woody biomass such as trees requires a process to obtain glucose from cellulose and hemicellulose, which requires a pretreatment for recovering sugars from the cellulose and hemicellulose, said pretreatment presenting problems of costs and handling. The present invention is based on the observation that koji fungus or yeast performs fermentation, directly from a tree degradation product, of the cellulose and/or carbohydrates alone in the tree, without feeding carbohydrates such as grain or bran.

Formation of tree degradation products is carried out by fractionating, via sieving with a mesh filter, a bulk degradation product obtained using mother cell lyases associated with sporulation of MRE symbiotic bacteria, followed by using the resultant powdery degradation product as a feedstock for a tree-fermentation. This route makes it easier to ferment with the flavor or the like intrinsic to the tree preserved therein while suppressing the antimicrobial strength held by the tree.

Next, after addition of water to the fermentation feedstock and its heat sterilization in an autoclave or a steamer, it is fed with koji fungus to perform a primary fermentation at 25° C. for four days, followed by removing solids from the resultant fermentation broth. The fermentation broth freed of solids, to which yeast is further added, is subjected to a secondary fermentation at 15° C. for a day. The fermentation broth obtained by the secondary fermentation is filtered through a filter to provide a final fermentation broth. Performing in this manner can provide a tree fermentation broth essentially free of isopropyl alcohol. This fermentation broth retains the flavor of the feedstock tree and/or some antibacterial components.

In order to make bamboo vinegar when using bamboo, for example, as a tree, a fermentation is allowed to continue as is for an over-fermentation, thereby yielding a bamboo vinegar containing no harmful components. Further, bamboo shochu liquor can be produced by distilling in the range 80° C. to 90° C. and blending the resultant distillate in with the secondary fermentation stock broth. The tree fermentation broth obtained by the secondary fermentation can be used as a seasoning with a tree flavor because it contains savory tasty components, glutamic acid and/or aspartic acid.

In further detail, the finely crushed trees to the size of about 1 cm to 5 mm obtained in the first stage, are degraded in a dry type degradation apparatus using the MRE. Said degradation apparatus makes use of lysosomal homologous degradative enzymes of mother cell lyases produced in an endospore formation step by the MRE symbiotic bacteria.

In this specification, said MRE symbiotic bacteria consist of *Bacillus* sp. (FERM BP-11209, Identification Number MK-005), *Lysinibacillus fusiformis* (FERM BP-11206, Identification Number MK-001), *Bacillus sonorensis* (Identification number MK-004), *Lysinibacillus* sp. (FERM BP-11207, Identification Number MK-002), and *Comamonas* sp. (FERM BP-11208, Identification Number MK-003), all of which are aerobic bacteria.

The method according to the present invention comprises filtering the solution after the formed endospores precipitated, through a 0.2 μm membrane and a 0.02 μm filter thereby removing an extremely minute amount of the remaining cultured cells and the remaining suspended endospores; and treating trees with the resultant solution which is obtained by aeration. This then led to the present inventors' discovery that alcohol can be produced from trees that could not have been used previously as a feedstock for alcohol because their degradation was difficult, resulting in the present invention.

In more detail, 1 m³ of the MRE symbiotic bacteria (MK-001, MK-002, MK003, MK-004, MK-005) culture medium, a group of aerobic bacteria that form said endospores, each thereof is placed in two 1.2 m³ culture aerator tanks of the same shape and aerated to reach the dissolved oxygen concentration of 0.5 mg/L to 1.2 mg/L. One of them was called the culture cell tank and the other the sporulation tank. The culture cell tank was fed with 500 g of fish meal, 500 g of rice bran, 250 g oil cake, and 50 g of broth as minimal nutrients; culturing was continued under culture conditions of pH 6.0 to 6.8 and an incubation temperature of 25° C. to 35° C. with an aeration applied thereto. On the other hand, the sporulation tank is placed under a starvation state with no nutrients added thereto at all, followed by continued aeration under conditions of 25° C. to 35° C., when triggered by the depletion of nitrogenous ingredients, the formation of endospores starts. After an increase in the clarity of the culture medium, the aeration (oxygen supply) is terminated, when the endospores begin to precipitate all at once to give a transparent solution. The solution was filtered through a 0.2 μm membrane and further a 0.02 μm filter, and the filtrate was placed again in a well-cleaned sporulation tank to get ready for a tree degradation. Herein, the filtrate which has been freed of the remaining mother cells and spores by filtration of the solution in which the MRC bacteria were allowed to form spores is called the MRE solution. Thus, the MRE solution is said to be in a state with hardly any bacteria or spores; and said MRE solution contains mother cell lyases. The present invention makes use of the degrading power of the mother cell lyases. Incidentally, the present specification may use expressions such as "MRE solution", "post sporulation solution," bacteria-free post sporulation solution" and the like, but unless it is particularly noted, all of these refer to a solution containing mother cell lyases.

In the present invention, the sizes of the membrane and filter applied to the above solutions are not particularly limited. For example the membrane may be of 1 μm, 0.7 μm, 0.5 μm, even 0.3 μm, preferably 0.2 μm. Further, the filter may be of 0.15 μm, 0.1 μm, 0.07 μm, 0.05 μm, or 0.03 μm, preferably 0.02 μm.

In addition, experiments as below are carried out in the present invention using the above-mentioned two, the culture cell tank and the sporulation tank, which are being aerated such that the dissolved oxygen concentration reaches 0.5 mg/L to 1.2 mg/L.

The MRE solution is effective if used at a temperature range of 60° C. to 80° C. Particularly it is preferred to spray the solution containing mother cell lyases in an environment where oxygen flows in at all times, and to degrade with stirring and heating, such that the subject tree is at not more than 80° C. using a heat dissipater plate, wherein said solution may contain spores along with the mother cell lyases. The apparatus operated under this principle is referred to as a dry type degradation apparatus using the MRE, which is capable of degrading, at temperatures as low as 80° C. or lower, trees that are not usually degradable, thereby allowing them to be used as a an alcoholic fermentation feedstock.

In the present invention said dry type degradation apparatus is used to degrade trees that present problems, such as bamboo, hinoki cypress, and sugi cedar, trees that have been weeded out and rice straw, so as to allow a feedstock for alcohol production to be made.

In the present invention, the MRE solution used for degrading trees maybe an undiluted or diluted solution, but it is preferably diluted 1 to 100 fold, more preferably diluted 1 to 50 fold, further preferably 1 to 25 fold, yet further preferably 1 to 10 fold, most preferably diluted 3 to 6 fold for use thereof.

In the present invention, crushed trees are treated with said dry type degradation apparatus, and after a passage of about 36 to 48 hours, they yield a fine powdery residue in a dry state with a 3.8% to 6% water content. The residue upon sieving with a designated mesh can give an MRE-treated tree powder. Because the MRE-treated tree powder is in a super dry state, it has characteristics of not readily absorbing moisture and of not rotting when left standing over a long period of time.

Further, in one embodiment according to the present invention, the degradation apparatus may also be divided into a degradation tank and a finish tank, so as to allow a pretreatment to be first carried out in the degradation tank and then the degradation to be completed in the finish tank. In this case the pretreatment in the degradation tank is carried out at 60 to 80° C., preferably at 70° C. for 36 to 48 hours, followed by adding water to the feedstock obtained in the degradation tank and carrying out the treatment in the finish tank at 60 to 80° C., preferably at 70° C. for 24 hours.

Further, in an embodiment according to the present invention, the tree as a feed for the fermentation can be immersed in a solution containing spores produced by sporulation of the mother cell lyases and/or said spore-forming aerobic bacteria, according to the present invention, and be degraded while the said solution is aerated.

Further, in the present invention, the size of the sieve applied to the above residue is not particularly limited. For example, it may be a 5 to 8 mm mesh or a 2 to 5 mm mesh, preferably a 1 mm mesh. The residue retained on the sieve can also be retreated in said degradation tank.

In addition, the MRE-treated tree powder (bamboo powder) according to one embodiment of the present invention, when analyzed, contained 43.1% of cellulose, 12.6% of hemicellulose, and 25.2% of lignin. The balance 19.1% was carbohydrates, proteins, and lipids.

In addition, in one embodiment of the present invention, the koji fungus used in the primary fermentation can be *Aspergillus amazake, Aspergillus orgzae* (NBRC30104), *Aspergillus orgzae* (NBRC30113), *Aspergillus cellulosae* (NBRC4040). *Aspergillus cellulosae* (IFO4297), *Aspergillus usami* (NBRC4033), and *Aspergillus awamori* (NBRC4388), but there is no limitation thereto, as long as it can saccharify a tree powder, and the rice koji fungus can also be used.

In addition, in one embodiment of the present invention, the yeast used for the secondary fermentation can be baker's yeast, *Saccharomyces celevisiae* (NBRC0244), *Saccharomyces celevisiae* (NBRC0249), *Saccharomyces celevisiae* (NBRC0282), *Saccharomyces celevisiae* (NBRC2373), *Saccharomyces celevisiae* (NBRC2377) and *Saccharomyces celevisiae* (IFO1728), but there is no limitation thereto, as long as it is a yeast capable of a conventional alcoholic fermentation.

Further, in one embodiment of the present invention, the alcoholic fermentation from a tree powder can be carried out by the following procedure. First, the MRE tree powder with added water at a ratio of 10 times by weight is sterilized in an autoclave at 120° C. for 15 minutes. A primary fermentation with a koji fungus such as amazake koji fungus or black koji fungus *Aspergillus oryzae* NBRC4388 is performed at 25° C. for 4 days. Next, the solids are removed from the product by the primary fermentation, and yeast is added thereto, to carry out the secondary fermentation at 15° C. for 1 day. The solution produced by the secondary fermentation subjected to a 0.45 μm filtration followed by a 0.2 μm filtration can yield a secondary fermentation product broth with not less than 0.29% alcohol concentration. The present invention is not limited to the procedures described above; optimum fermentation conditions (such as temperature and duration) can be appropriately selected in accordance with the type of koji fungus and yeas used, wherein it is also possible to use the conventional alcoholic fermentation or shochu liquor making procedures.

Further, in one embodiment of the present invention, it was found that the secondary fermentation product broth of the present invention, as analyzed by gas chromatography, is an ethanol containing very little isopropyl alcohol, which is undesirable for beverages. Furthermore, the secondary fermentation product broth of the present invention contains umami (tasty) components called free aspartic acid and free glutamic acid, the same as those of kelp seaweed. Therefore, use, as a seasoning, of the secondary fermentation product broth of the present invention makes it possible to provide a seasoning with a tree flavor containing an extremely small amount of ethanol, free aspartic acid, and free glutamic acid.

Continuing the secondary fermentation for performing over-fermentation converts ethanol to 100% acetic acid. The over-fermentation provides a tree-flavored acetic acid containing the umami (tasty) ingredients called free aspartic acid and free glutamic acid. A table vinegar of any acetic concentration can be prepared by adding acetic acid obtained by distillation of the tree acetic acid.

Further, in one embodiment of the present invention, shochu liquor with a tree flavor can be prepared by continuously distilling the secondary fermentation product broth of the present invention at 79° C. to 90° C., thereby extracting ethanol and adding thereto within 2% of the secondary fermentation product broth so as to adjust the alcohol concentration to 20% to 40%. Further, in one embodiment of the present invention, a seasoning derived from the tree components can also be obtained by heating to concentrate the residual solution resulting from the continuous distillation to obtain shochu liquor, thereby elevating the concentrations of umami (tasty) components such as glutamic acid and/or aspartic acid.

Further, in the present invention, trees such as bamboo, hinoki cypress, and sugi cedar as an alcoholic fermentation feedstock can be used, but there is no particular limitation as long as it is a tree that has been difficult to ferment because it contains antimicrobial substances by the conventional methods.

In one embodiment of the present invention, the fermentation residues obtained by removing the alcohol after fermentation can also be used as an agricultural compost. Heretofore, it has been problematically difficult to process the residues from fermentation processes, such as for shochu liquor, from the standpoints of environmental protection, along with incurred high processing costs as well. The fermented residue resulting in the present invention can also be used as a good agricultural compost and/or for animal feeds.

Hereinafter, an embodiment and examples according to the present invention will be explained with reference to the drawings.

EXAMPLES

Example 1

Production of an MRE Solution

Culturing MRE symbiotic bacteria are carried out according to a common culturing method for aerobic gram-positive bacteria. A 1.2 cubic meter culture aeration tank is charged with 1000 liters of water and aerated. The culture aeration tank is fed with 3 kg of fish meal, 3 kg of rice bran, 1.6 kg of oil cake, and 350 g of broth as nutrients, along with appropriate amounts of minerals such as magnesium sulfate and silica. Then the bacterial cells are added thereto to culture the MRE symbiotic bacteria under culturing conditions of a culture pH 6.0 to 6.8 and culture temperature of 25° C. to 35° C., along with an aeration being applied so as to maintain the dissolved oxygen concentration at 0.5 mg/L to 1.2 mg/L.

On reaching a sufficient bacterial growth and stabilization, all the nutrients for the MRE symbiotic bacteria are stopped so as to be placed under a starvation state, followed by a further aeration under a condition of 15° C. to 35° C., when the depletion of the nitrogenous ingredients triggers starting the formation of endospores of the MRE symbiotic bacteria. After the clarity of the culture medium increases all at once, the aeration is stopped, when the endospores begin to precipitate, concurrently resulting in a transparent supernatant broth.

The supernatant thus obtained, when further pressure-filtered through a 0.2μ membrane, yields an MRE solution. The timing to stop the aeration can also be checked out with a phase contrast microscope thereby assuring that the sporulation has completed.

Example 2

Method for Producing an MRE-Treated Bamboo

The bamboo used in the present Example is that which has been treated with the MRE solution according to procedures 1 to 5 as below.

1. Use 60 L of sieve retained fraction of bamboo for a floor material.
2. Feed the degradation tank with 40 L of bamboo that has been crushed for the floor material and the MRE solution; and carry out a degradation treatment at 70° C. for 36 hours.
3. After 36 hours, take out the feedstock from the degradation tank and measure the volume and weight.
4. Add 20 L water to what was taken out of the degradation tank, and place it into the finish tank.
5. Treat for 24 hours in the finish tank at 70° C. (not more than 8% moisture) and sieve with a 1 mm mesh sieve. Re-feed the sieve retained fraction to the step 2.

This flow is shown below:
Method for Production of MRE-Treated Bamboo

Example 3

Alcoholic Fermentability Test Using Baker's Yeast
Experimental materials are as follows.
MRE enzyme treated bamboo powder (1 mm mesh sieve)
Pulverized raw bamboo (1 mm mesh sieve)
Mineral water ("Morinomizudayori" Sold by Coca Cola)
Amazake-koji fungus (*Aspergillus amazake*)
Dry yeast (Product of Nissin Foods Co., Ltd., Nissin Super Cameria)

(1) Method of Fermentation Using Yeast

Raw bamboo and the MRE-treated bamboo, 125 g each, were thoroughly stirred with 250 g of water (mineral water). This was followed by autoclaving to heat-treat (121° C., 15 min), cooling to room temperature, adding 5 g of dry yeast and 400 ml of sterile mineral water as a feed water (hereafter called feed water), mixing well, and performing an alcoholic fermentation at 15° C. for three days. After the end of the fermentation, the broth was wrung out with cotton fabric and distilled in a pot still, followed by measuring the alcohol concentration. FIG. 1A shows an alcoholic fermentation flow of raw bamboo; FIG. 1B, an alcoholic fermentation flow of the MRE-treated bamboo.

Figure 2:
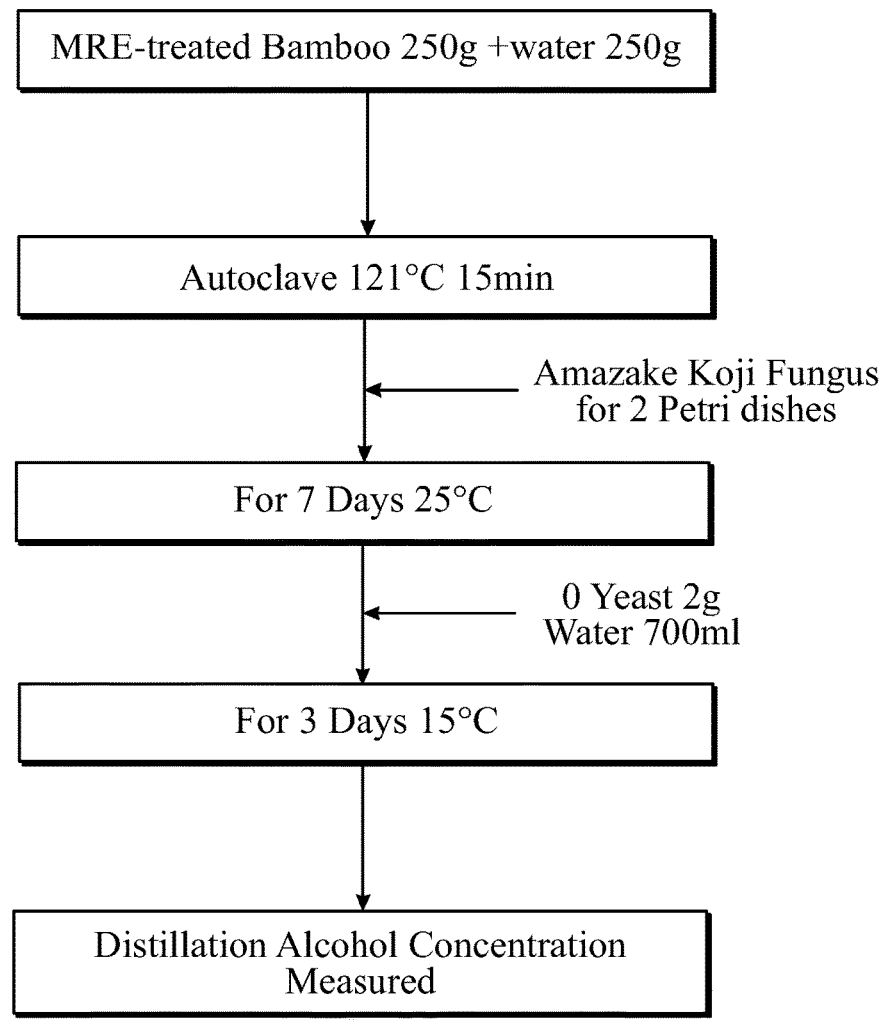
FIG. 2 is a flow sheet for an alcoholic fermentation after saccharification in one embodiment of the present invention.

The Method for Saccharification and Fermentation 250 g of the MRE-treated bamboo, was thoroughly stirred with 250 ml of mineral water. This was followed by autoclaving to heat-treat (121° C., 15 min), cooling to room temperature, adding amazake koji fungus for a primary fermentation, and allowing to stand at 25° C. for 7 days. Then for a secondary fermentation, 2 g of dry yeast and 700 ml of sterile water (mineral water) were added, followed by thoroughly mixing and carrying out an alcoholic fermentation at 15° C. for three days. After the end of the fermentation, the broth was wrung out with cotton fabric and distilled in a pot still, followed by measuring the alcohol concentration. FIG. 2 shows a flow of the alcoholic fermentation flow of the experimental method.

Example 4

Growth test of koji fungus used in the primary fermentation and alcoholic fermentation study.

Experimental materials and strains used are as follows.

MRE enzyme-treated bamboo powder (1 mm mesh sieve)

Mineral water ("Morinomizudayori" Sold by Coca Cola)

TABLE 1

Strains Used

| Aspergillus amazake |  | White |
| Aspergillus orgzae | NBRC30104 | Koji |
| Aspergillus orgzae | NBRC30113 | Fungus |
| Aspergillus cellulosae | NBRC4040 | Yellow |
| Aspergillus cellulosae | IFO4297 | Koji Fungus |
| Aspergillus usami | NBRC4033 | Black |
| Aspergillus awamori | NBRC4388 | Koji Fungus |

(1) Mycelial Growth Test, by Koji Fungus Type.

Mineral water was added to the MRE-treated bamboo, and 20 g each of the 80% hydrated material was equally distributed into Petri dishes. This was followed by autoclaving (121° C., 15 min) for a heat treatment, then cooling, and inoculating with a total of 7 strains, respectively: three white koji fungus types (*Aspergillus amazake*, *Aspergillus orgzae* NBRC 30104, NBRC30113); two yellow koji fungus types (*Aspergillus cellulosae* NBRC4040, IFO4297); and two black koji fungus types (*Aspergillus usami* NBRC4033, and *Aspergillus awamori* NBRC4388), growing at 25° C. for 10 days, and studying a mycelial growth.

(2) Mycelial Growth Test by % Hydration.

A mycelial growth test by % hydration was conducted using the koji fungi that gave good results in the mycelial growth test, by koji fungus type. Mineral water was added to the MRE-treated bamboo to give 60%, 80%, and 100% hydrated materials, respectively, and 20 g each of them was equally distributed into Petri dishes. This was followed by autoclaving (121° C., 15 min) for a heat treatment, cooling, inoculating with koji fungi, growing at 25° C. for 10 days, and studying a mycelial growth.

Figure 3:
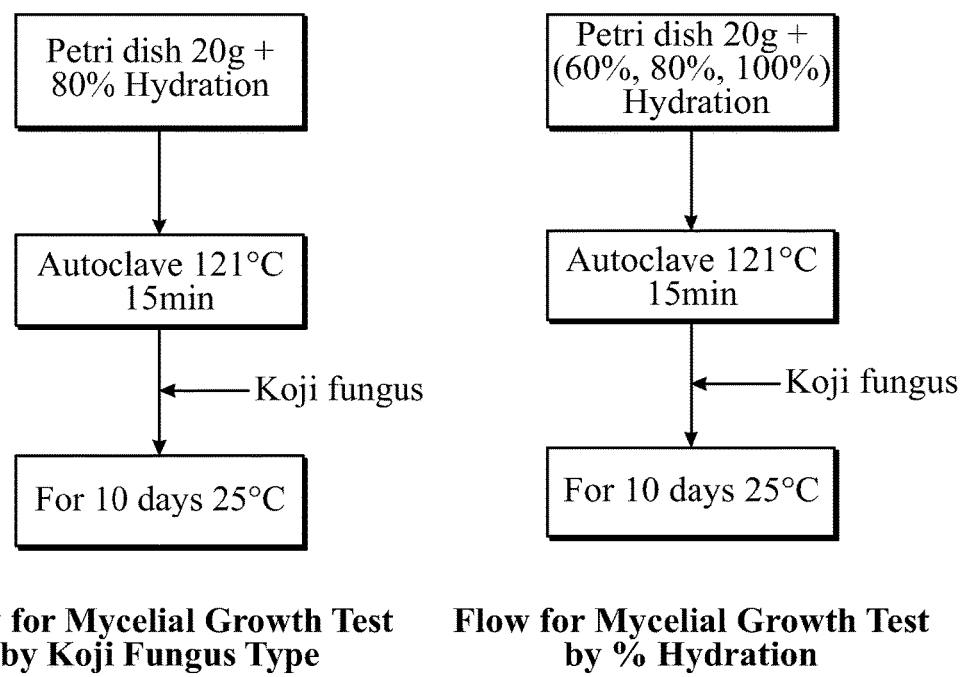
FIG. 3 is a flow sheet for a mycelial growth test in one embodiment of the present invention.

FIG. 3A shows the mycelial growth test flow by koji fungus type; FIG. 3B, the mycelial growth test flow by % hydration.

Example 5

Study of Alcoholic Fermentation Conditions

Experimental materials are as follows.

MRE enzyme-treated bamboo powder (1 mm mesh sieve)

Mineral water ("Morinomizudayori" Sold by Coca Cola)

Amazake-koji fungus (*Aspergillus amazake*)

Dry yeast (Product of Nissin Foods Co., Ltd., Nissin Super Cameria)

Gas chromatography (GC) measurement conditions

Alcohol concentration measurement: gas chromatography by GL Sciences Inc. was used.

Measurement conditions are shown in the table below.

TABLE 2

GC Measurement Condition

| GC | |
| --- | --- |
| Column: | gaskuropack54 60/80, 2 m × 3 mm I.D, Col. temp: 180° C. |
| Carrier Gas: | He 0.4 Mpa |
| Injection: | 200° C., Splitless 1 uL |
| Detection: | FID 10 × 3, 200° C. |

Method for Studying Alcoholic Fermentation Conditions.

Figure 4:
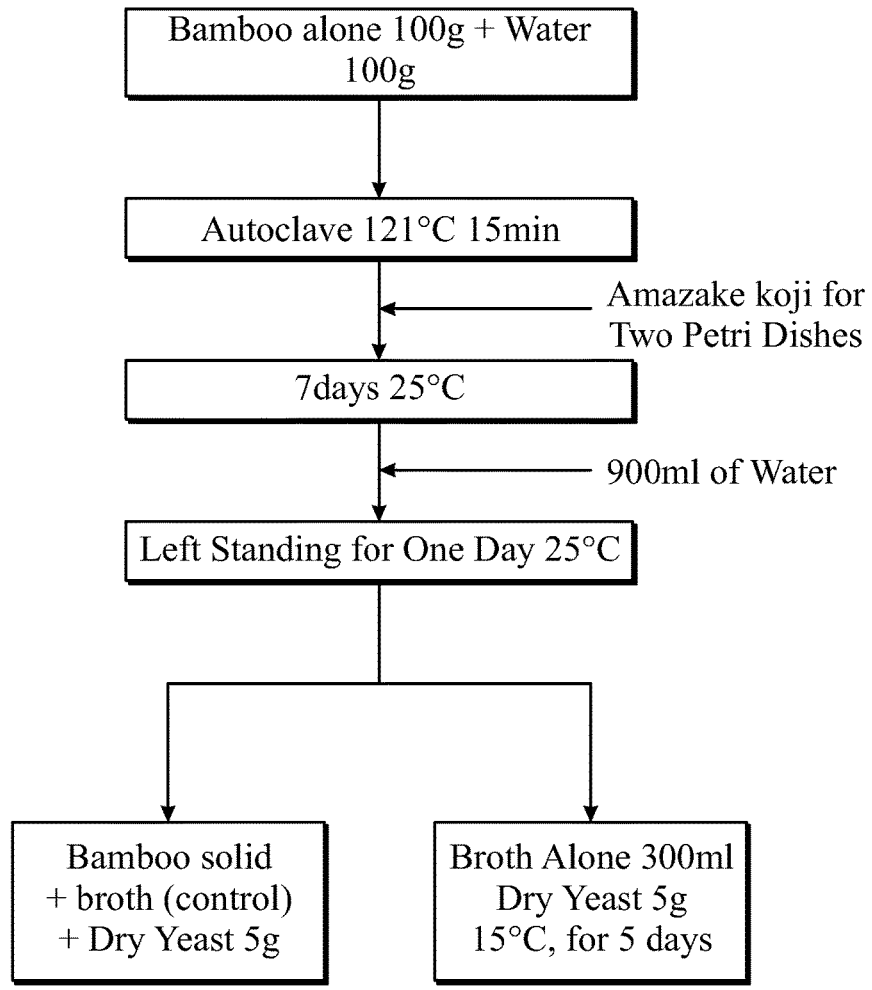
FIG. 4 is a flow sheet for studying the alcoholic fermentation conditions in one embodiment of the present invention.

100 g of the MRE-treated bamboo was thoroughly stirred with 100 ml of mineral water added thereto. This was followed by autoclaving (121° C., 15 min), cooling, adding amazake koji fungus, stirring well, and fermenting at 25° C. for 7 days (primary fermentation). Then, 900 ml of feed water was added, followed by mixing well and letting stand for one day. Thereafter, 300 ml of the liquid alone was fractionated into a 500 ml beaker, thereby separating into the liquid alone and bamboo solid powder+liquid (control), respectively, which were subjected to secondary fermentation. The conditions for the secondary fermentation called for adding 5 g of dry yeast, stirring well, and then stirring every other day for 5 days. FIG. 4 shows the flow of the experimental method.

Example 6

Study of the Yeast Suitable for Alcoholic Fermentation

Experimental materials and yeasts used are as follows.

MRE enzyme-treated bamboo powder (1 mm mesh sieve)

Mineral water ("Morinomizudayori" Sold by Coca Cola)

Strains Used:

The strain for the primary fermentation: *Aspergillus amazake* (Isolated from Ikeya Brewery Partnership Co.'s Amazake (sweet sake) koji fungus)

Yeasts used: Seven yeast types for an alcoholic fermentability study)

TABLE 3

7 Yeast Types for Alcoholic Fermentability Condition Study

| Product of Nissin Foods, Inc | Dry Yeast (Baker's Yeast) |
| --- | --- |
| Saccharomyces celevisiae | NBRC0244 (JAPAN sake-moto) |
| Saccharomyces celevisiae | NBRC0249 (JAPAN sake-moto) |
| Saccharomyces celevisiae | NBRC0282 (JAPAN shocyu-moromi) |
| Saccharomyces celevisiae | NBRC2373 (JAPAN Awamori-kawachi) |
| Saccharomyces celevisiae | NBRC2377 (Sake yeast Kyokai No. 9) |
| Saccharomyces celevisiae | IFO1728 (indonesia fermenting-cacao) |

Medium Used

The composition of the medium used (PD broth medium) is as follows.

Potato Starch 4.0 g/L

Dextrose 20.0 g/L

The above-mentioned medium composition was used for the broth culturing of the yeasts. Further, the agar medium was used by adding agar to the above medium composition to reach 1.5% thereof.

Kit Used

Use was made of a Glucose CII-Test Wako, a glucose assay kit made by Wako Junyaku Kogyo Co. The operating method followed the Kit's operating procedure. The calculation of the glucose concentration used the following formula.

Glucose concentration (g/L)=Absorbance($Es$)/
0.0001×0.001

Gas Chromatography (GC) Measurement Conditions

The measurement conditions are as shown in the table below.

TABLE 4

| GC Measurement Condition | |
|---|---|
| GC | |
| Column: | gaskuropack54 60/80, 2 m × 3 mm I. D, Col. temp: 180° C. |
| Carrier Gas: | He 0.4 Mpa |
| Injection: | 200° C., Splitless 1 uL |
| Detection: | FID 10 × 3, 200° C. |

High Performance Liquid Chromatography (HPLC) Measurement Conditions

Measurement conditions for glucose concentration using an Agilent Technologies Co's HPLC are as follows.

HPLC Measurement Conditions
HLPC
Column: TSK-GEL AMIDE-80HR,
TSKgel G2500PWXL,
TSKguardcolumn PWXL
Column Temp: 40° C.
Eluent: $H_2O$
Flow rate: 0.5 mL/min
Detector: RI 35° C.
Splitless: 20 μL
Experimental Method FIG. 5 shows the flow of the experimental method.

200 g of mineral water was added to 200 g of the MRE-treated bamboo, followed by autoclaving at 121° C. for 15 min. After the mixture was cooled to room temperature, about 0.1 g of *A. amazake* as a seed koji fungus was added, followed by mixing well to allow standing fermentation at 25° C. for 7 days, which is designated primary fermentation. The primary fermentation product was thoroughly mixed with 1800 ml of sterile water (mineral water) added thereto and was left standing for 24 hrs. After 24 hours, the supernatant was distributed in 100 ml each into 300-ml volume beakers.

18φ test tubes holding the above mentioned PD culture medium were inoculated with a platinum loop of yeasts shown in Table 3 respectively and incubated at 30° C. and 100 cpm for 24 hrs. This was designated a pre-culture medium, 1% of the pre-culture medium was respectively inoculated into a 500 ml volume Erlenmeyer flask (working volume with 200 ml of the PD medium) and was incubated at 30° C. and 100 cpm for 24 hrs; this was designated a main culture medium. After 24 hrs, 200 ml of the main culture was centrifuged using a small size refrigerated centrifuge (TOMY Co., Ltd.) at 4° C. and 8 krpm for 10 minutes to give cultured yeast. The total amount of the cultured yeast was suspended in 3 ml of sterile water and added to the primary fermentation broth, thereby starting a secondary fermentation. The secondary fermentation was conducted at 15° C. for 3 days under standing condition with a gentle stirring every 24 hours. During the secondary fermentation the alcohol concentration was measured every 24 hrs using a GC (made by GL Sciences Inc.) and the glucose concentration was measured at Day 0 and 3 days later using an HPLC (made by Tosoh Co.). Use was made of the primary fermentation broth to which no yeast was added, as a control.

Figure 5:
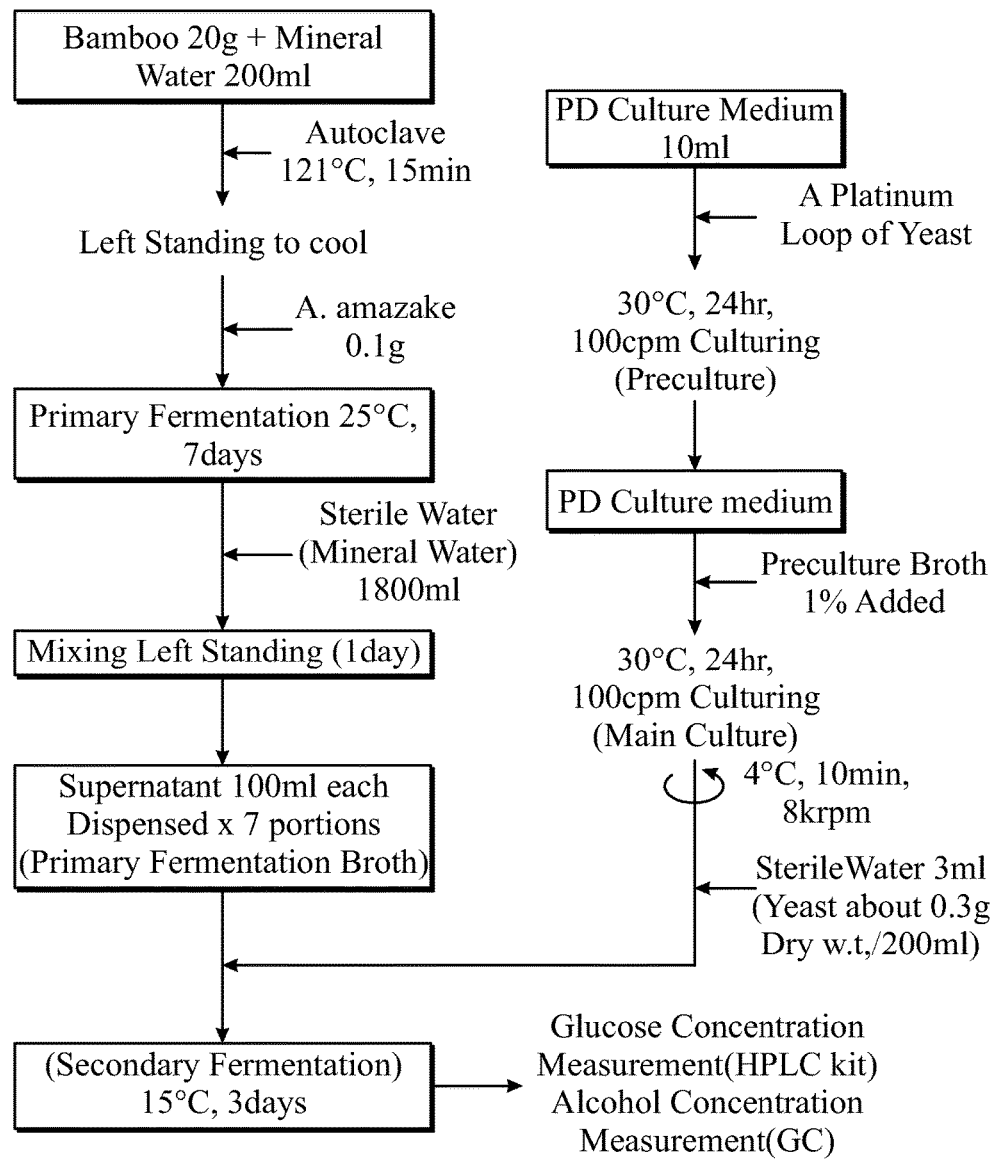
FIG. 5 is a flow sheet for studying the alcoholic fermentability, by yeast, in one embodiment of the present invention.

The experiment was twice repeated according to the flow sheet shown in FIG. 5. The yeasts used in the second study are shown in the table as follows.

TABLE 5

| Yeasts for Second Alcoholic Fermentability Study 4 Types | |
|---|---|
| Product of Nissin Foods, Inc | Dry Yeast (Baker's Yeast) |
| *Saccharomyces celevisiae* | NBRC0244 (JAPAN sake-moto) |
| *Saccharomyces celevisiae* | NBRC0249 (JAPAN sake-moto) |
| *Saccharomyces celevisiae* | NBRC2373 (JAPAN Awamori-kawachi) |

In the second study, the measurement of the alcohol concentration was the same as that of the first study; the measurement of glucose concentration every 24 hrs, used the above glucose kit for the measurement, 3 times: Day 0, Day 1, and Day 3 with a combined use of the kit and the HPLC.

Example 7

Study of Alcohol Fermentation by a Stage Feeding

Experimental materials are as follows.

MRE enzyme-treated bamboo powder (1 mm mesh sieve)

Mineral water ("Morinomizudayori" Sold by Coca Cola)

Amazake-koji fungus (*Aspergillus amazake*)

Dry yeast (Product of Nissin Foods Co., Ltd., Nissin Super Cameria)

Figure 6:
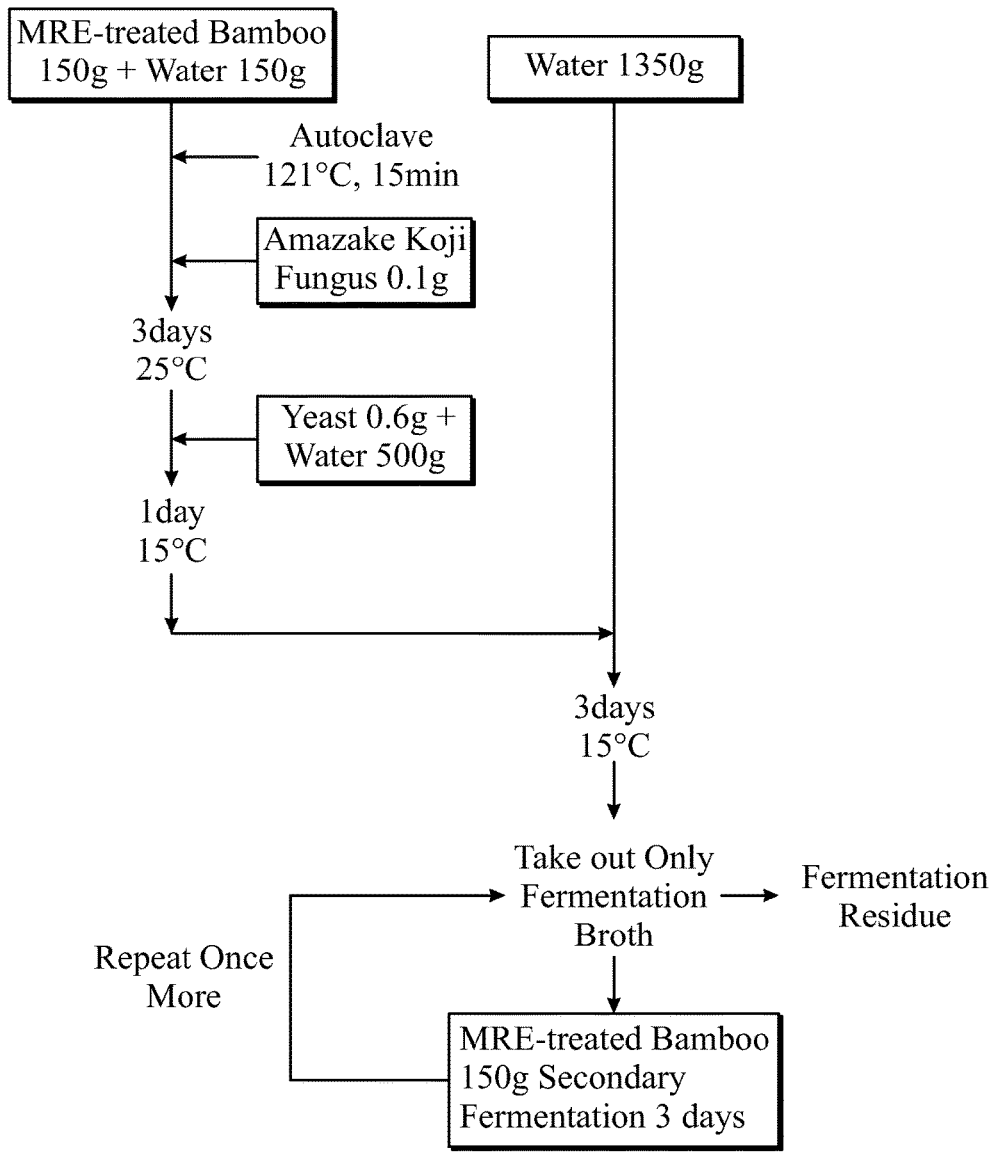
FIG. 6 is a flow sheet for stage feeding of the MRE-treated bamboo in one embodiment of the present invention.

Experimental Method (1) Stage Feeding of MRE-Treated Bamboo 150 g of water (mineral water) was added to 150 g of MRE-treated bamboo in a stainless steel kettle, and mixed well. This was followed by autoclaving at 121° C. for 15 min, cooling to room temperature, then adding about 0.1 g of *A. amazake*, and stirring well so as to uniformly mix the fungus. This was left standing at 25° C. for 3 days. It was gently stirred once a day and was designated the primary fermentation feedstock upon confirming that the mycelia have grown sufficiently over the entire MRE-treated bamboo. Thereafter, 500 g of feed water and 0.6 g of shochu liquor yeast (*Sacharromyces celevisiae* NBRC0249) were added, and the mixture was thoroughly stirred. This was left standing at 15° C. for 1 day, followed by adding 1200 g of feed water, mixing well, and standing at 15° C. for 3 days; and thereafter only the fermentation broth was taken out. 150 g of the primary fermentation feedstock was added to this fermentation broth as a second stage feeding, followed by standing at 15° C. for 3 days. Once again, only the fermentation broth was taken out and 150 g of the primary fermentation feedstock was added thereto as a third stage feeding, followed by standing at 15° C. for 3 days. During the time, the mixture was gently stirred every day, and a visual observation of the state of the fermentation and measurement of the alcohol concentration were performed. The measurement of the alcohol concentration was made with GC. FIG. 6 shows the flow sheet, and Table 6 the fed materials.

TABLE 6

| List of Fed Materials | | | |
|---|---|---|---|
| | First Stage Feeding | Second Stage Feeding | Third Stage Feeding |
| MRE-treated Bamboo | 150 g | 150 g | 150 g |
| Rice Koji Fungus | — | — | — |
| Feed Water | 2000 g | 0 g | 300 g |

Figure 7:
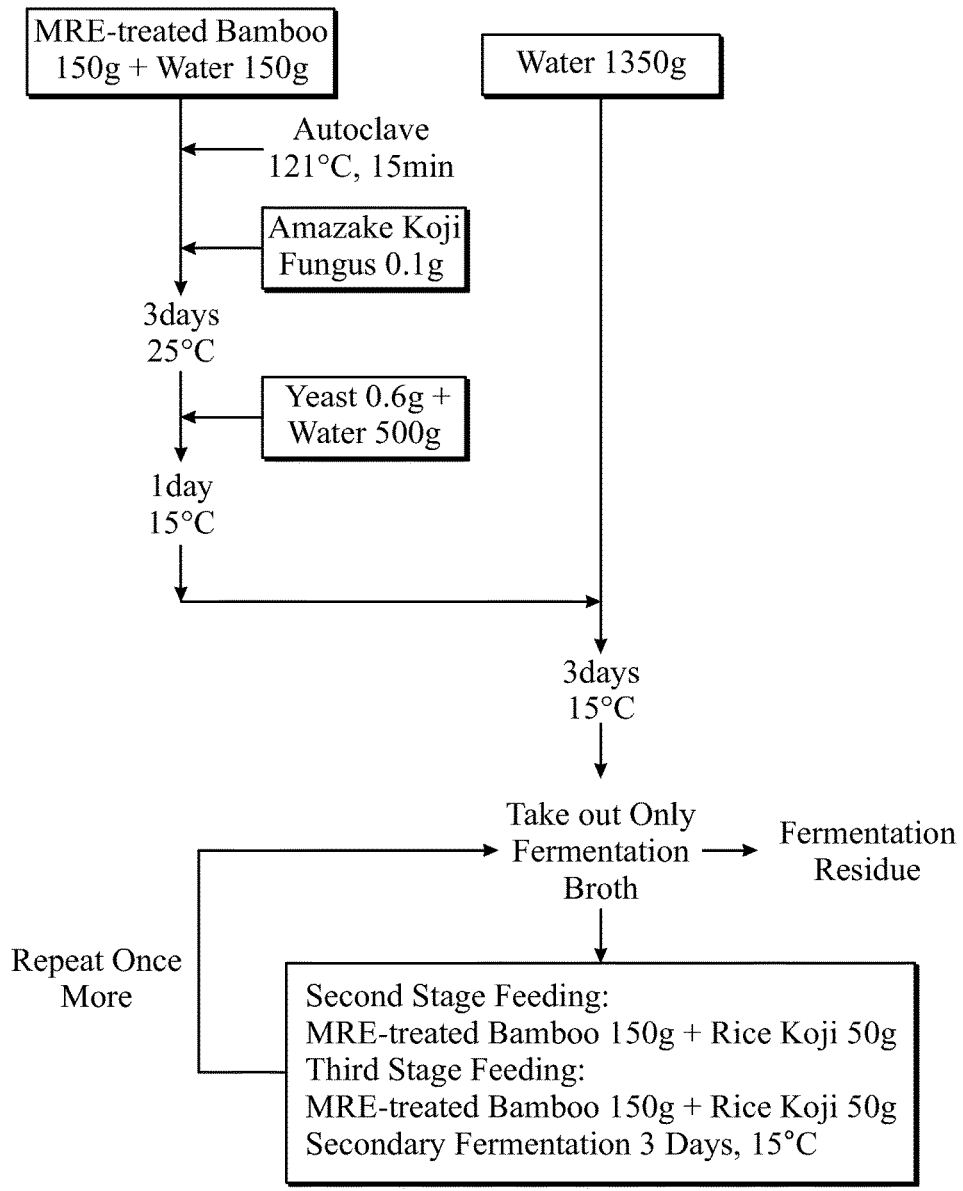
FIG. 7 is a flow sheet for stage feeding of the MRE-treated bamboo with uniformly mixed rice koji fungus in one embodiment of the present invention.

(2) Stage Feeding of MRE-Treated Bamboo with Rice Koji Fungus Uniformly Mixed Therein 150 g of water (mineral water) was added to 150 g of MRE-treated bamboo and mixed well. This was followed by autoclaving at 121° C. for 15 min, cooling to room temperature, then adding about 0.1 g of *A. amazake*, and stirring well so as to uniformly mix the fungus. This was left standing at 25° C. for 3 days. It was gently stirred once a day and was designated the primary fermentation feedstock upon confirming that the mycelia have grown sufficiently over the entire MRE-treated bamboo. Then, 500 g of feed water and 0.6 g of shochu liquor yeast (*Sacharromyces celevisiae* NBRC0249) were added thereto, and the mixture was thoroughly stirred. This was left standing at 15° C. for 1 day followed by adding 50 g of rice koji fungus and 1350 g of feed water, mixing well and standing at 15° C. for 3 days; and then only the fermentation broth was taken out. The primary fermentation feedstock and 50 g of rice koji fungus were added to this fermentation broth as a second stage feeding, followed by standing at 15° C. for 3 days. Once again, only the fermentation broth was taken out, followed by adding, as the third stage feeding, the primary fermentation feedstock, 50 g of rice koji fungus, and 300 ml of feed water, and standing at 15° C. for 3 days. During the time, the mixture was gently stirred every day, and a visual observation of the state of the fermentation and measurement of the alcohol concentration were performed. The measurement of the alcohol concentration was made with GC. FIG. 7 shows the flow sheet and Table 7, the fed materials.

TABLE 7

| List of Fed Materials | | | |
|---|---|---|---|
| | First Stage Feeding | Second Stage Feeding | Third Stage Feeding |
| MRE-treated Bamboo | 150 g | 150 g | 150 g |
| Rice Koji Fungus | 50 g | 50 g | 50 g |
| Feed Water | 2000 g | 0 g | 300 g |

(3) A Stage Feeding of MRE-Treated Bamboo with a Step-by-Step Decremental Rice Koji Fungus.

Figure 8:
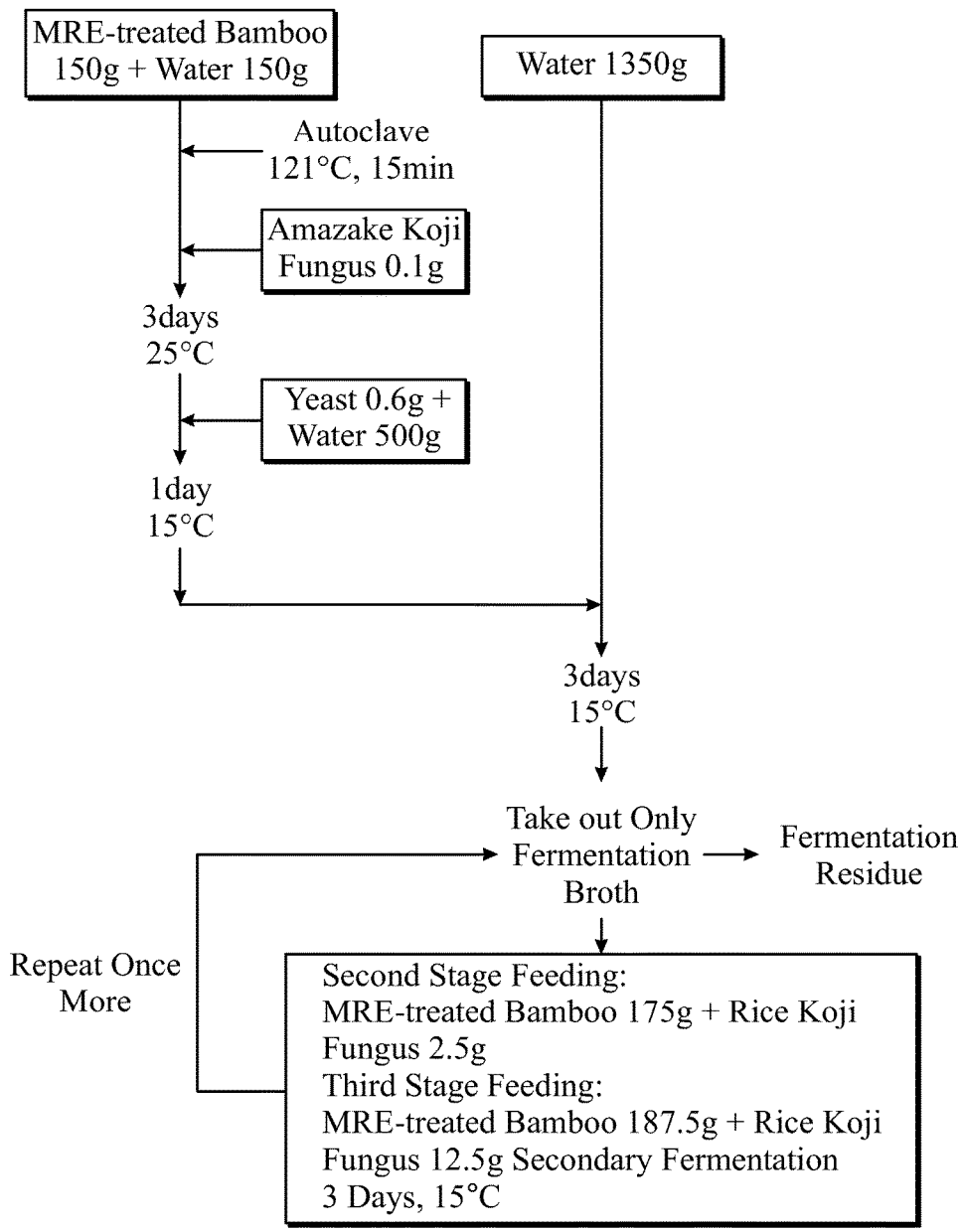
FIG. 8 is a flow sheet for stage feeding of the MRE-treated bamboo with a step-by-step decremental rice koji fungus in one embodiment of the present invention.

150 g of water (mineral water) was added to 150 g of MRE-treated bamboo in a stainless-steel kettle and mixed well. This was followed by autoclaving at 121° C. for 15 min, cooling to room temperature, then adding about 0.1 g of *A. amazake*, and stirring well so as to uniformly mix the fungus. This was left standing at 25° C. for 3 days. It was gently stirred once a day and was designated the primary fermentation feedstock upon confirming that the mycelia have grown sufficiently over the entire MRE-treated bamboo. Then, 500 g of feed water and 0.6 g of shochu liquor yeast (*Sacharromyces celevisiae* NBRC0249) were added thereto, and the mixture was left standing at 15° C. for 1 day followed by adding 1,350 g of feed water, mixing well and standing at 15° C. for 3 days, and then only the fermentation broth was taken out. 175 g of the primary fermentation feedstock and 25 g of rice koji fungus were added to the fermentation broth as a second stage feeding, followed by standing at 15° C. for 3 days. Once again, only the fermentation broth was taken out; and 187.5 g of the primary fermentation feedstock, 12.5 g of rice koji fungus, and 500 g of feed water were added thereto as a third stage feeding, followed by standing at 15° C. for 3 days. During the time, the mixture was gently stirred every day, and a visual observation of the state of the fermentation and measurement of the alcohol concentration were performed. The measurement of the alcohol concentration was made with GC. FIG. 8 shows the flow sheet, and Table 8 the fed materials.

TABLE 8

| List of Fed Materials | | | |
|---|---|---|---|
| | First Stage Feeding | Second Stage Feeding | Third Stage Feeding |
| MRE-treated Bamboo | 150 g | 175 g | 187.5 g |
| Rice Koji Fungus | 50 g | 25 g | 12.5 g |
| Feed Water | 2000 g | 0 g | 500 g |

Figure 9:
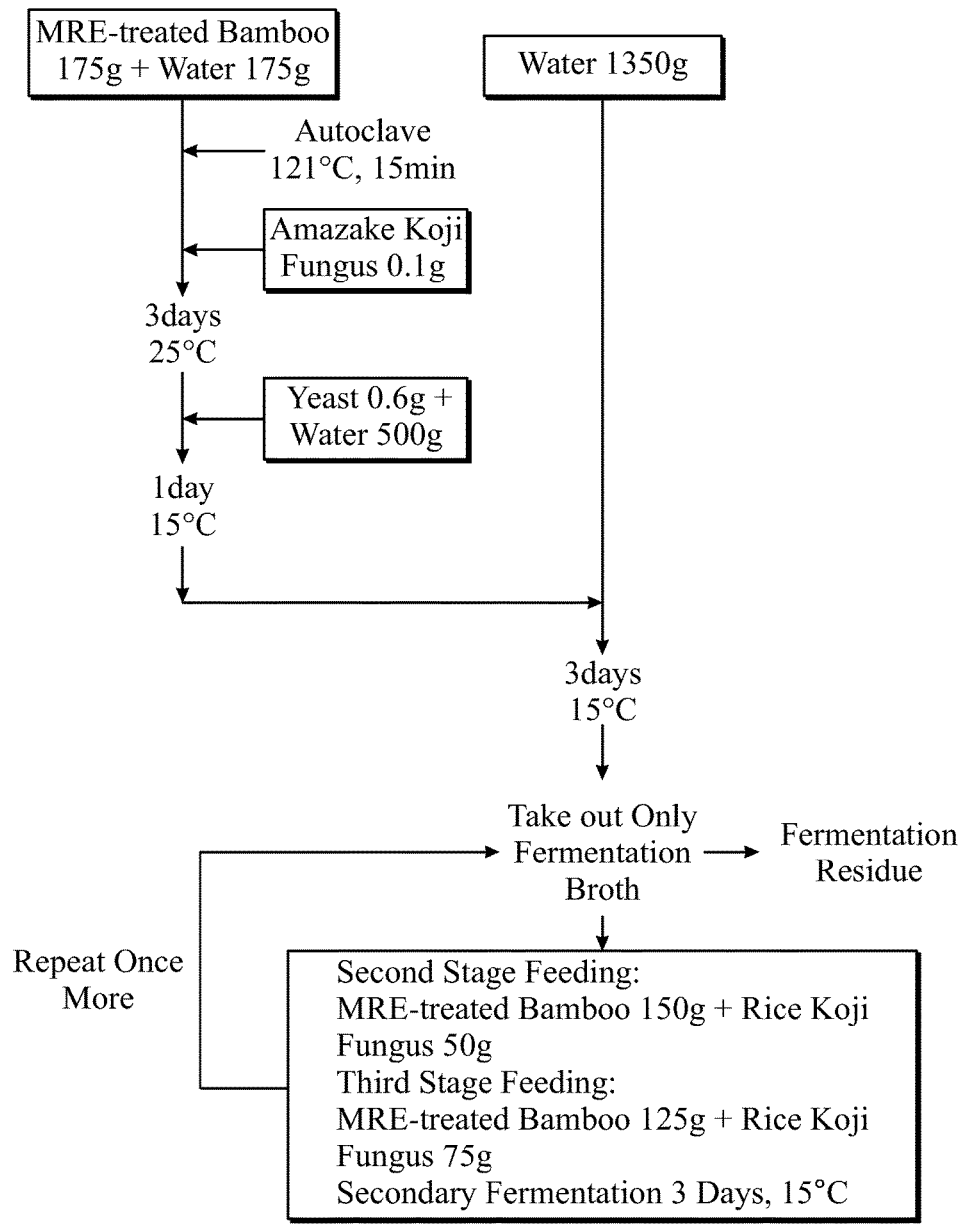
FIG. 9 is a flow sheet for stage feeding of the MRE-treated bamboo with a step-by-step incremental rice koji fungus in one embodiment of the present invention.

A stage feeding of MRE-treated bamboo with a step-by-step incremental rice koji fungus (4) 175 g of water (mineral water) was added to 175 g of MRE-treated bamboo in a stainless-steel kettle, and mixed well. This was followed by autoclaving at 121° C. for 15 min, cooling to room temperature, then adding about 0.1 g of *A. amazake*, and stirring well so as to uniformly mix the fungus. This was left standing at 25° C. for 3 days. It was gently stirred once a day and was designated the primary fermentation feedstock upon confirming that the mycelia have grown sufficiently over the entire MRE-treated bamboo. Then, 500 g of feed water and 0.6 g of shochu liquor yeast (Sacharromyces celevisiae NBRC0249) were added thereto, and the mixture was stirred well. This was left standing at 15° C. for 1 day followed by adding 1325 g of sterile water, mixing well and standing at 15° C. for 3 days, and then only the fermentation broth was taken out. 150 g of the primary fermentation feedstock and 50 g of rice koji fungus were added to this fermentation broth as a second stage feeding, followed by standing at 15° C. for 3 days. Once again, only the fermentation broth was taken out and 125 g of the primary fermentation feedstock and 75 g of rice koji fungus were added thereto as a third stage feeding, followed by standing at 15° C. for 3 days. During the time, the mixture was gently stirred every day, and a visual observation of the state of the fermentation and measurement of the alcohol concentration were performed. The measurement of the alcohol concentration was made with gas chromatography. FIG. 9 shows the flow sheet and Table 9 the fed materials.

TABLE 9

| List of Fed Materials | | | |
|---|---|---|---|
| | First Stage Feeding | Second Stage Feeding | Third Stage Feeding |
| MRE-treated Bamboo | 175 g | 150 g | 125 g |
| Rice Koji Fungus | 25 g | 50 g | 75 g |
| Feed Water | 2000 g | 0 g | 0 g |

Example 8

Study of Large Volume Alcoholic Fermentation

Experimental materials are as follows.

MRE enzyme-treated bamboo powder (1 mm mesh sieve)
Mineral water ("Morinomizudayori" Sold by Coca Cola)
Amazake-koji fungus (*Aspergillus amazake*)
Dry yeast (Product of Nissin Foods Co., Ltd., Nissin Super Cameria)

Figure 10:
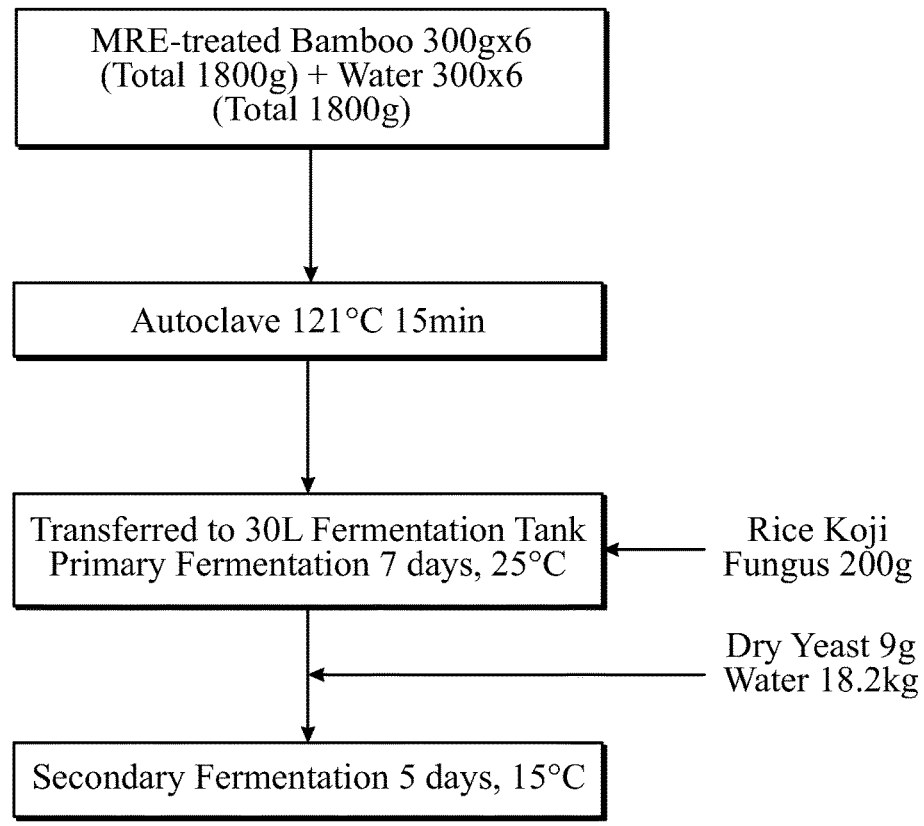
FIG. 10 is a flow sheet of a large volume fermentation experiment for the MRE-treated bamboo in one embodiment of the present invention.
Figure 11:
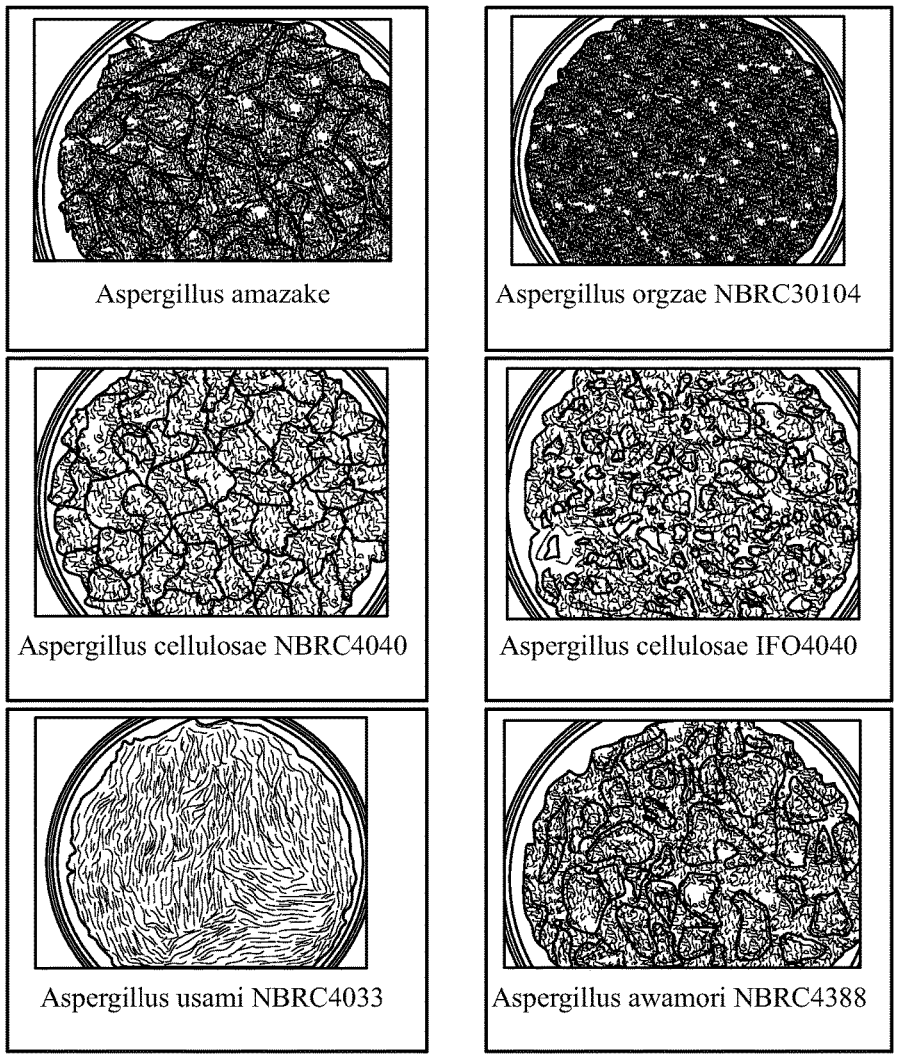
FIG. 11 is Day 10 photographs of a mycelial growth test, by koji fungus type in one embodiment of the present invention.

Experimental Method 300 g (a total of 1.8 kg) each of MRE-treated bamboo powder was measured off into 6 steel kettles and 300 g each (a total of 1.8 kg) of mineral water was added thereto, followed by stirring well and mixing and then autoclaving for a heat treatment at 121° C. for 15 min. 1.8 kg of the heat treated sample was transferred to a 30 L volume fermentation tank, followed by adding 200 g of rice koji fungus and mixing, stirring every 24 hrs, allowing growth at 25° C. for 7 day, and designating this as a primary fermentation. After the primary fermentation, 18.2 kg of feed water and 9 g of dry yeast were added, followed by stirring well, allowing alcoholic fermentation to take place, and designating this as the secondary fermentation. The alcohol concentration and glucose concentration during the secondary fermentation were measured every other day. The flow sheet is shown in FIG. 10.

Results (1) Alcoholic Fermentability Tests Using Baker's Yeast

The following Table shows the results of alcoholic fermentation of, using only yeast, of raw bamboo and the MRE-treated bamboo, after its saccharification treatment with *A. amazake* as the primary fermentation.

TABLE 10

Results of Alcohol Concentration Measurement Under Various Conditions

|  | Alcohol Concentration (%) |
|---|---|
| Raw Bamboo | 0.04 |
| MRE-treated Bamboo | 0.06 |
| MRE-treated Bamboo Saccharified with *A. amazake* | 0.23 |

In the results obtained, the alcohol concentration was the lowest, 0.04%, with the raw bamboo, next 0.06%, with the MRE-treated bamboo, and highest, 0.23%, with the MRE-treated bamboo that has been treated for saccharification using *A. amazake* as the primary fermentation.

(2) Growth Test of Koji Fungus Used in the Primary Fermentation

Table 11 shows the results of mycelial growth test by koji fungus type; FIG. 1 the Day 10 photographs.

TABLE 11

Visual Inspection Results of Mycelial Growth Test by Koji Fungus Type

|  | Day 5 | Day 7 | Day 10 |
|---|---|---|---|
| Amazake | Δ Only Around the Fungus Body | ◯ Spread Entirely over MRE-treated Bamboo Surface | ◉ The Fungus Body Spread Entirely in Petri Dish with Colony Formation |
| NBRC 30104 | X | Δ Only Around the Fungus Body | ◯ Spread Entirely over MRE-treated Bamboo Surface |
| NBRC 4040 | X | X | Δ Grew a Little only Around the Fungus body |
| IFO 4297 | X | X | Δ Grew on Largish MRE-treated Bamboo Fragments |
| NBRC 4033 | X | X | X |
| NBRC 4388 | X | Δ Only Around the Fungus Body | Δ Entire Spreading is Slow |

Figure 12:
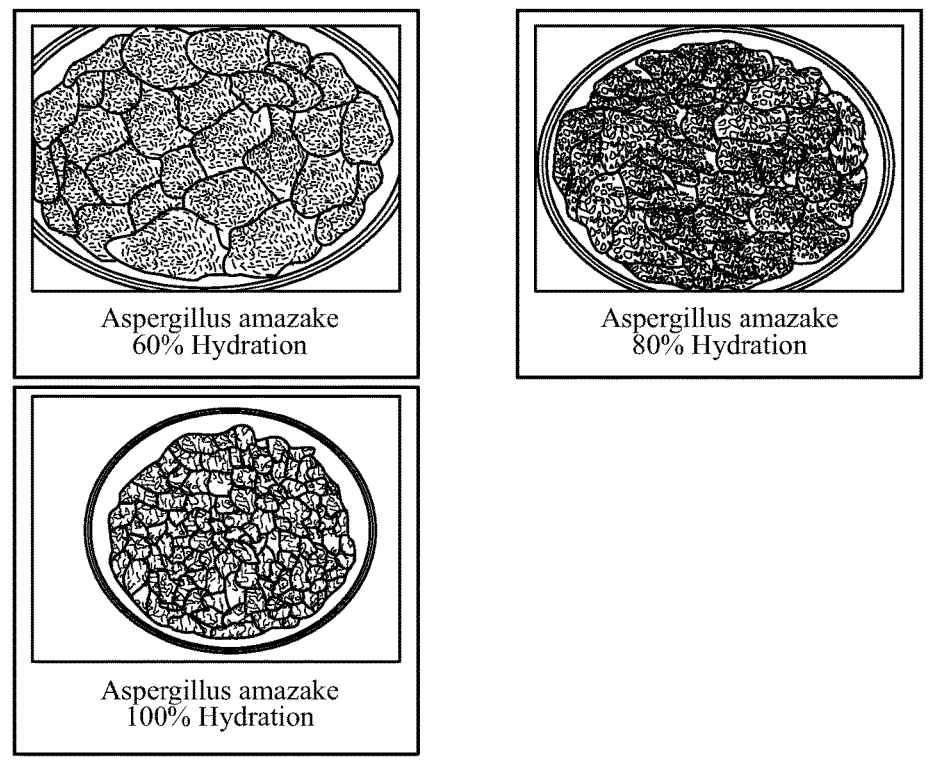
FIG. 12 is Day 10 photographs of a mycelial growth test, by % hydration in one embodiment of the present invention.

In addition, Table 12 shows the results of the mycelial growth test by % hydration; FIG. 12 the Day 10 photographs.

TABLE 12

|  | Day 3 | Day 5 | Day 7 | Day 10 |
|---|---|---|---|---|
| Visual Inspection Results of Mycelial Growth Test at 60% Hydration ||||| 
| *Aspergillus amazake* | Δ Only Around the Fungus Body | Δ Only Around the Fungus Body | ◯ Spread Entirely over MRE-treated Bamboo Surface | ◯ Spread Entirely over MRE-treated Bamboo Surface |
| Visual Inspection Results of Mycelial Growth Test at 80% Hydration |||||
| *Aspergillus amazake* | Δ Only Around the Fungus Body | ◯ Spread Entirely over MRE-treated Bamboo Surface | ◯ Spread Entirely over MRE-treated Bamboo Surface | ◉ The Fungus Body Spread Entirely in Petri Dish with Colony Formation on surface |
| Visual Inspection Results of Mycelial Growth Test at 100% Hydration |||||
| *Aspergillus amazake* | ◯ Spread Entirely over MRE-treated Bamboo Surface | ◉ The Fungus Body Spread Entirely in Petri Dish | ◉ The Fungus Body Spread Entirely in Petri Dish with Colony Formation on surface | ◉ The Fungus Body Spread Entirely in Petri Dish with Colony Formation on surface |

Table 11 shows that the *A. amazake* allowed the mycelia to grow at as early a stage as Day 5, with its mycelial growth still good at Day 10. Among the koji fungi, white koji fungus showed a good growth, and the next in growth were two yellow koji fungus types and black koji fungus *A. usami* NBRC4033, both equally good. No mycelial growth was observed with black koji fungus, *A awamori* RC4388.

For a mycelial growth test by change in % hydration, the test was conducted with *A. Amazake* that showed the best mycelial growth in the koji fungus type, by fungus type.

In the mycelial growth test by % hydration, Table 12 showed that the mycelial growth was in order hydration 100%>80%>60%. At 100% hydration, the mycelial growth over the entire MRE-treated bamboo was observed at a stage as early as Day 5.

(3) Study of Alcoholic Fermentation Conditions

Table 13 shows the results of the alcoholic fermentation of a saccharified bamboo broth alone and Table 14 the alcoholic fermentation with the MRE-treated bamboo solid added thereto (control).

TABLE 13

Fermentation with Broth Alone Using Saccharified Bamboo

| | Alcohol Concentration (%) |
|---|---|
| Day 1 | 0.18 |
| Day 2 | 0.20 |
| Day 3 | 0.17 |
| Day 5 | 0.21 |

TABLE 14

Fermentation with Bamboo + Broth (control)

| | Alcohol Concentration (%) |
|---|---|
| Day 1 | 0.10 |
| Day 2 | 0.13 |
| Day 3 | 0.08 |
| Day 5 | 0.12 |

Tables 13 and 14 reveal that the alcohol concentration of the broth alone was higher than the control for all the dates, Day 1, Day 2. Day 3, and Day 5. The alcohol concentration with the broth alone was highest at 0.21%, while the alcohol concentration with the control was highest on Day 2 at 0.13%.

(4) Study of the Yeast Suitable for Alcoholic Fermentation

Figure 13:
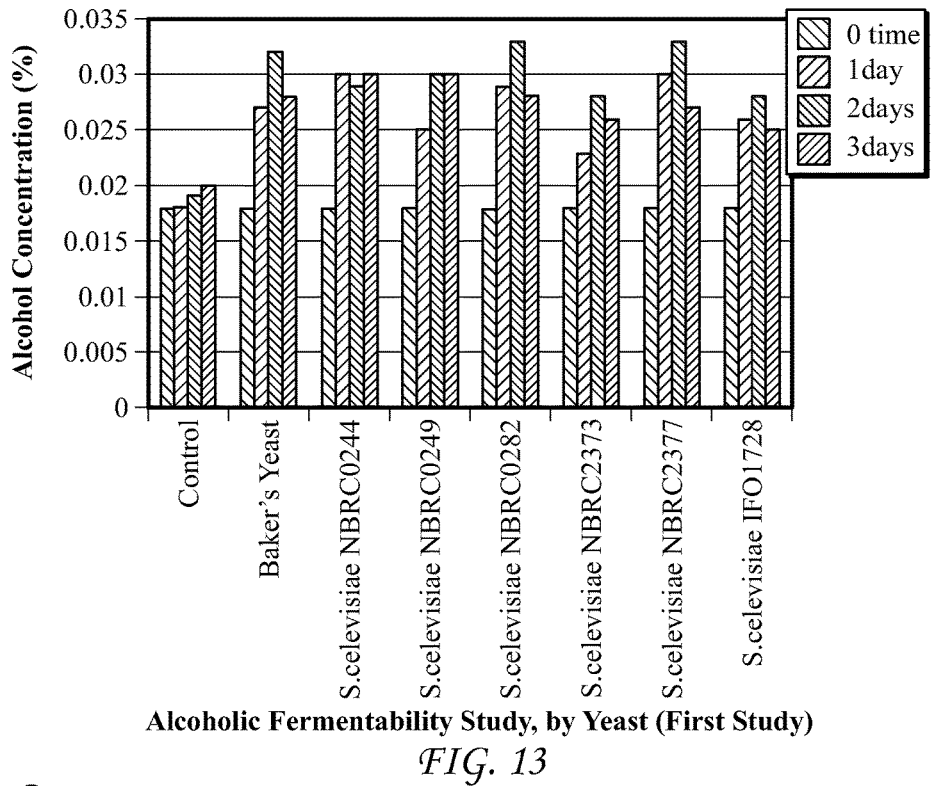
FIG. 13 is a graph showing the results, by yeast, of a first alcoholic fermentability test in one embodiment of the present invention.
Figure 14:
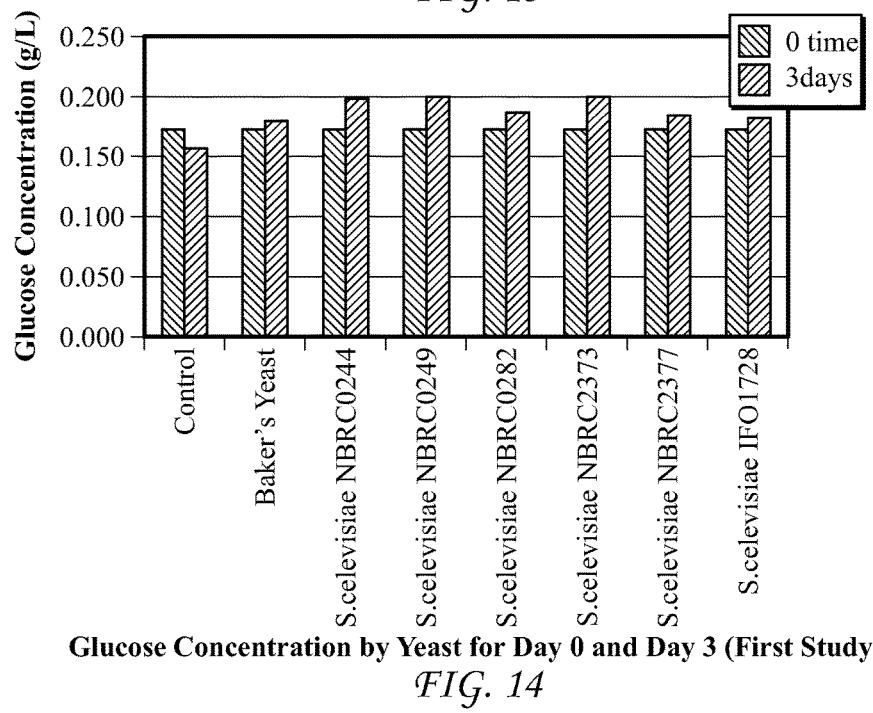
FIG. 14 is a graph showing a glucose concentration in one embodiment of the present invention.

Table 15 and FIG. 13 show the results, by yeast, of the first alcoholic fermentability study; and FIG. 14 the glucose concentration.

TABLE 15

Alcoholic Fermentability Study Result, by Yeast (First Study)

| | Control | Baker's yeast | S. celevisiae NBRC0244 | S. celevisiae NBRC0249 | S. celevisiae NBRC0282 | S. celevisiae NBRC2373 | S. celevisiae NBRC2377 | S. celevisiae IFO1728 |
|---|---|---|---|---|---|---|---|---|
| Day 0 | 0.018 | 0.018 | 0.018 | 0.018 | 0.018 | 0.018 | 0.018 | 0.018 |
| Day 1 | 0.018 | 0.027 | 0.030 | 0.025 | 0.029 | 0.023 | 0.030 | 0.026 |
| Day 2 | 0.019 | 0.032 | 0.029 | 0.030 | 0.033 | 0.028 | 0.033 | 0.028 |
| Day 3 | 0.02 | 0.028 | 0.030 | 0.030 | 0.028 | 0.026 | 0.027 | 0.025 |
| Notes | | | Flavor ○ Fragrant (Coffee fragrance) | Flavor ○Sake-like Fragrance | Soy-sauce-ike Fragrance | Flavor ○ Sake-like Fragrance | Flavor Soft and Fragrant (Barley Tea Fragrance) | Weak Flavor Tree-honeydew-Fragrance |

Those that showed high alcohol concentration values were baker's yeast. *S. celevisiae* NBRC0282, and NBRC2377 (FIG. 13). However, in terms of flavor, as shown in Table 15, sake yeast cerevisiae NBRC0249 and shochu liquor yeast celevisiae NBRC2373 tended to be superior.

Figure 15:
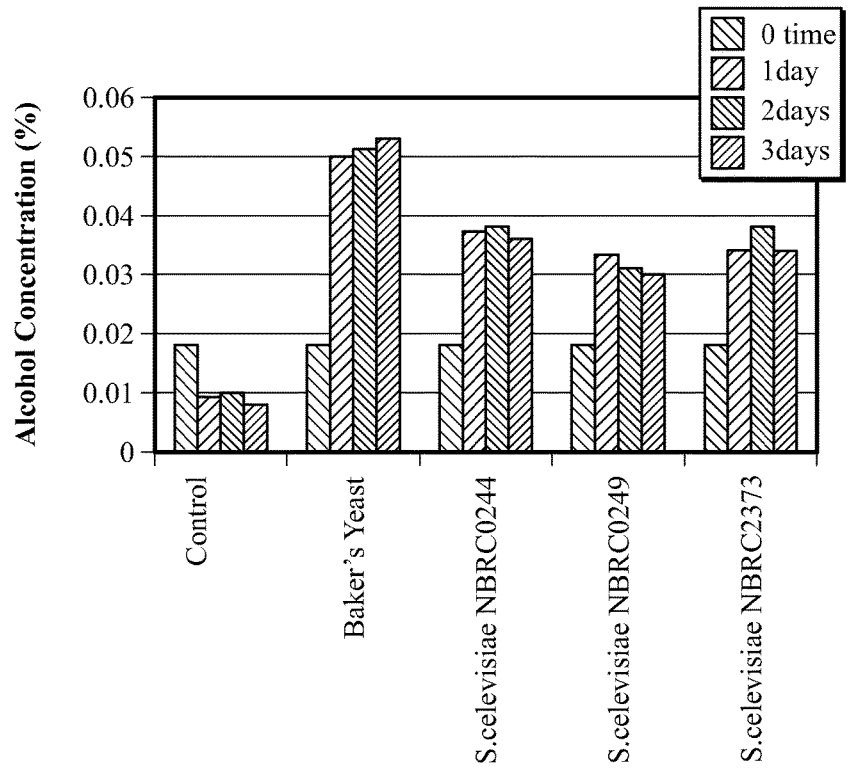
FIG. 15 is a graph showing the results, by yeast, of a second alcoholic fermentability test in one embodiment of the present invention.

With each yeast used in the study, on Day 2 fermentation, the alcohol concentration reached a steady state or tended to fall (see FIG. 14 and Table 15). In the glucose concentration of FIG. 1, the glucose concentration did not fall even on Day 3, with all data having suggested an increase. This led to a second study, with baker's yeast and selected three strains with good flavors from the 7 yeast strains, in accordance with the flow sheet shown in FIG. 5. In order to examine the trend in glucose concentration, it was decided then to make the measurement every 24 hours using the glucose kit. FIG. 15 shows the results of the second alcohol fermentability study; and FIG. 16 the glucose concentration.

Figure 16:
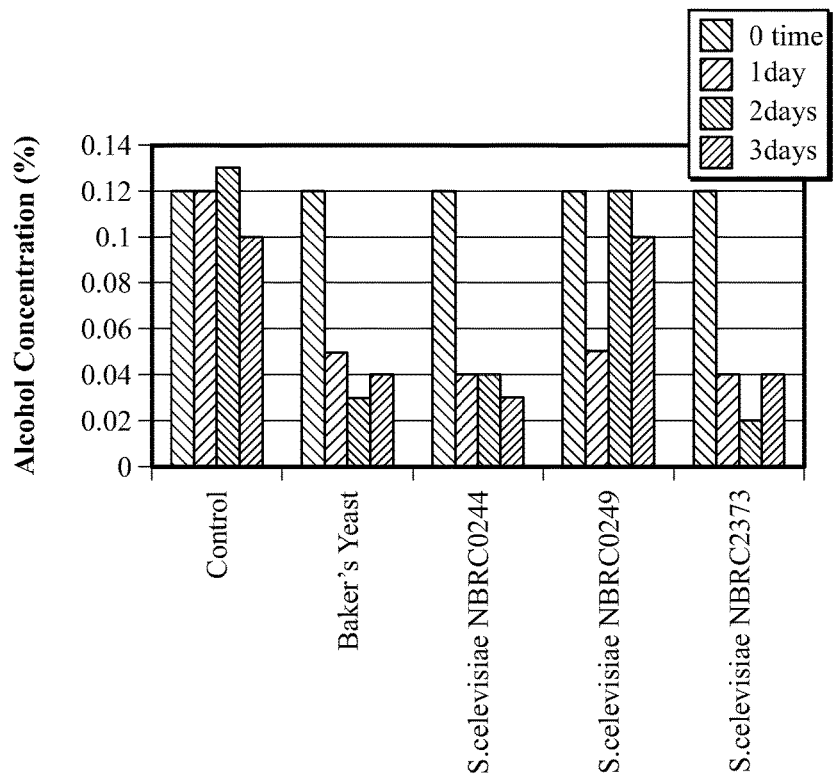
FIG. 16 is a graph showing a glucose concentration in one embodiment of the present invention.

As a result, a decrease in the glucose concentration was observed as the alcohol concentration increased (see FIGS. 15 and 16). It was noted that glucose was assimilated and converted significantly from Day 0 to Day 1 into alcohol, but on Day 2 and after, the glucose assimilation ability slackened. Further, when reaching Day 3 it was seen that the glucose concentration increased and the alcohol concentration decreased.

Study of Glucose Assimilation by Yeast (Second Study)

Table 16 shows results of measurement with HPLC.

TABLE 16

Second Glucose Assimilation Study, by Yeast (HPLC)

| | | | | | Unit (g/L) |
|---|---|---|---|---|---|
| | Control | Baker's Yeast | S. celevisiae NBRC0244 | S. celevisiae NBRC0249 | S. celevisiae NBRC2373 |
| Day 0 | 0.147 | 0.147 | 0.147 | 0.147 | 0.147 |
| Day 1 | 0.141 | 0.092 | 0.107 | 0.118 | 0.089 |
| Day 3 | 0.150 | 0.131 | 0.149 | 0.178 | 0.110 |

Similarly to FIG. 16, the results of measurement with HPLC also showed a decrease on Day 1 and an increase on Day 3, in glucose concentration.

Figure 17:
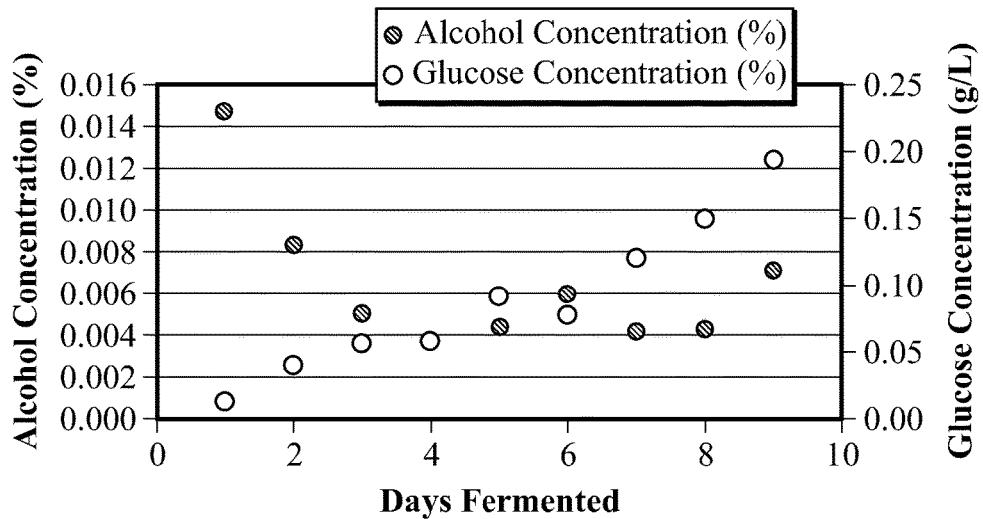
FIG. 17 is a graph showing the results of alcoholic fermentation carried out according to the method of the present invention and the glucose concentration in one embodiment of the present invention.

(5) Study of Alcoholic Fermentation with Stage Feeding (5-1) Stage Feeding of MRE-Treated Bamboo Alone Table 17 and FIG. 17 show the results of alcoholic fermentation according to the flow sheet, and the glucose concentration.

TABLE 17

9 Day Alcoholic Fermentation with Stage Feeding of MRE-treated Bamboo alone and Glucose Concentration (Before Distillation)

| Number of Feedings | Alcoholic Fermentation, Days | Alcohol Concentration (%) | Glucose Concentration (g/L) |
|---|---|---|---|
| 1 | Day 1 | 0.015 | 0.01 |
| | Day 2 | 0.008 | 0.04 |
| | Day 3 | 0.005 | 0.06 |
| 2 | Day 4 | 0.004 | 0.06 |
| | Day 5 | 0.004 | 0.09 |
| | Day 6 | 0.006 | 0.08 |

TABLE 17-continued

9 Day Alcoholic Fermentation with Stage Feeding of MRE-treated Bamboo alone and Glucose Concentration (Before Distillation)

| Number of Feedings | Alcoholic Fermentation, Days | Alcohol Concentration (%) | Glucose Concentration (g/L) |
|---|---|---|---|
| 3 | Day 7 | 0.004 | 0.12 |
|   | Day 8 | 0.004 | 0.15 |
|   | Day 9 | 0.007 | 0.19 |

As a result, the alcohol concentration was highest at 0.015% on alcoholic fermentation Day 1 and stayed at 0.004 to 0.008% thereafter (see Table 17 and FIG. 17). Table 17 reveals that the glucose concentration increased steadily with each passing day. Since the alcohol concentration was low, distillation was not performed.

(5-2) Stage Feeding with Rice Koji Fungus Uniformly Mixed with MRE-Treated Bamboo.

Figure 18:
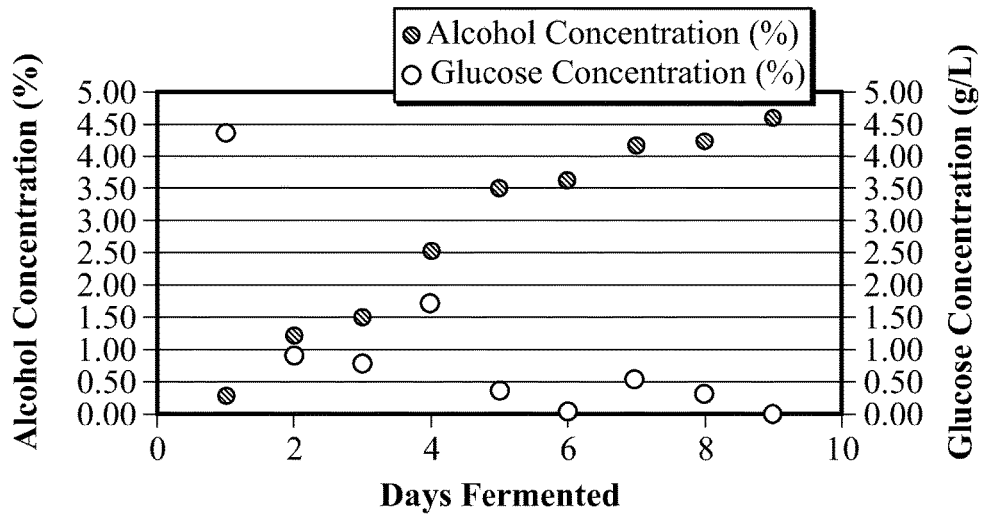
FIG. 18 is a graph showing the results of alcoholic fermentation carried out according to the method of the present invention and the glucose concentration in one embodiment of the present invention.

Table 18 and FIG. 18 show the results of alcoholic fermentation performed according to the flow sheet, and the glucose concentration.

TABLE 18

9 Day Alcohol Concentration with Stage Feeding of MRE-treated Bamboo along with Rice Koji Fungus Uniformly Mixed Therein And Glucose Concentration (Before Distillation)

| Number of Feedings | Alcoholic Fermentation, Days | Alcohol Concentration (%) | Glucose Concentration (g/L) |
|---|---|---|---|
| 1 | Day 1 | 0.28 | 4.40 |
|   | Day 2 | 1.15 | 0.93 |
|   | Day 3 | 1.51 | 0.77 |
| 2 | Day 4 | 2.53 | 1.71 |
|   | Day 5 | 3.50 | 0.41 |
|   | Day 6 | 3.58 | 0.00 |
| 3 | Day 7 | 4.15 | 0.54 |
|   | Day 8 | 4.24 | 0.30 |
|   | Day 9 | 4.55 | 0.00 |

As a result, an increase in the alcohol concentration is observed along with a concomitant reduction in the glucose concentration (see Table 18 and FIG. 18). The alcohol concentration was 0.28% on Day 1 and increased to as high as 4.55% on the last day (Day 9) in the third stage feeding, where the corresponding glucose concentration ended up 0%.

(5-3) Stage Feeding with a Step-by-Step Decremental Rice Koji Fungus to MRE-Treated Bamboo.

Figure 19:
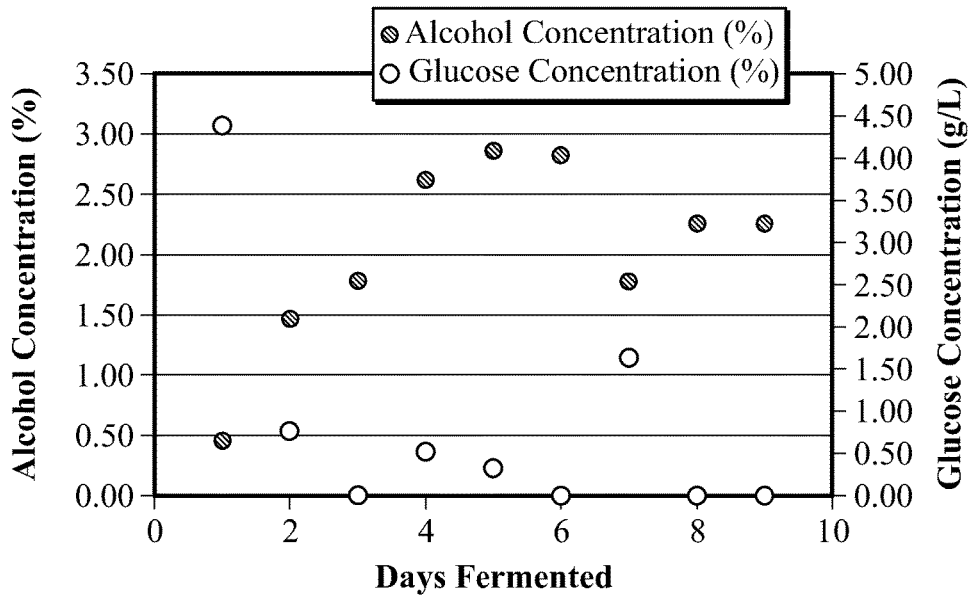
FIG. 19 is a graph showing the results of alcoholic fermentation carried out according to the method of the present invention and the glucose concentration in one embodiment of the present invention.

Table 19 and FIG. 19 show the results of alcoholic fermentation performed according to the flow sheet, and the glucose concentration.

TABLE 19

9 Day Alcohol Concentration of Stage Feeding of MRE-treated Bamboo with Step-by-step Decremental Rice Koji Fungus Thereto and Glucose Concentration (Before Distillation)

| Number of Feedings | Alcoholic Fermentation, Days | Alcohol Concentration (%) | Glucose Concentration (g/L) |
|---|---|---|---|
| 1 | Day 1 | 0.46 | 4.40 |
|   | Day 2 | 1.47 | 0.77 |
|   | Day 3 | 1.79 | 0.01 |
| 2 | Day 4 | 2.63 | 0.53 |
|   | Day 5 | 2.86 | 0.34 |
|   | Day 6 | 2.82 | 0.00 |
| 3 | Day 7 | 1.78 | 1.63 |
|   | Day 8 | 2.26 | 0.00 |
|   | Day 9 | 2.26 | 0.00 |

As a result, an increase in the alcohol concentration is observed along with a concomitant reduction in the glucose concentration (see Table 19 and FIG. 19). The alcohol concentration on Day 1 was 0.46% and was seen to decrease with an increase in the glucose concentration, once, in the third stage feeding. However, the alcohol concentration increased to as high as 2.26% on the last day (Day 9) of the third the stage feeding, where the glucose concentration ended up 0%. In addition, the number of days for the glucose concentration to fall to 0% became shorter as the amount of the rice Koji fungus dropped.

(5-4) Stage Feeding with a Step-by-Step Incremental Rice Koji Fungus to MRE-Treated Bamboo.

Figure 20:
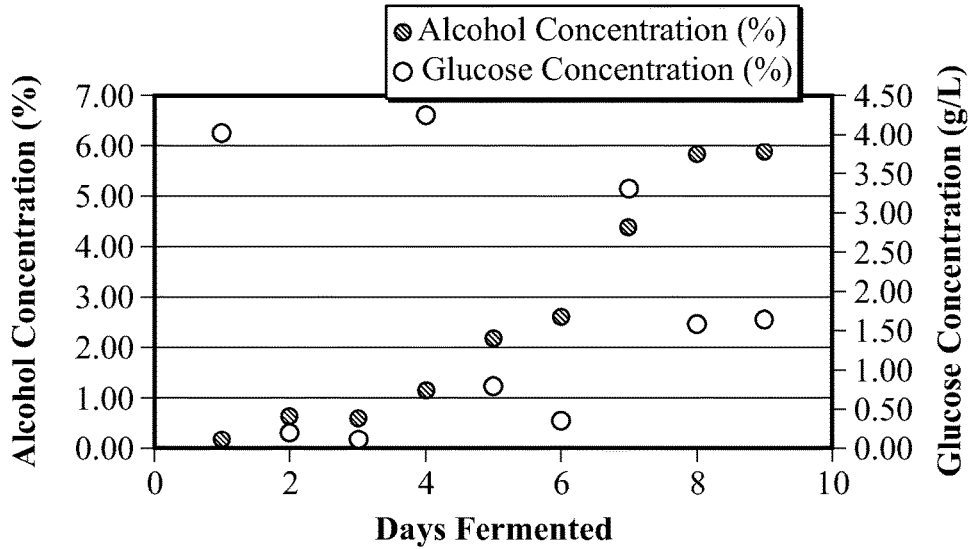
FIG. 20 is a graph showing the results of alcoholic fermentation carried out according to the method of the present invention and the glucose concentration in one embodiment of the present invention.

Table 20 and FIG. 20 show the results of alcoholic fermentation performed according to the flow sheet, and the glucose concentration.

TABLE 20

9 Day Alcohol Concentration of Stage Feeding of MRE-Created Bamboo with Step-by-step Incremental Rice Koji Fungus Thereto and Glucose Concentration (Before Distillation)

| Number of Feedings | Alcoholic Fermentation, Days | Alcohol Concentration (%) | Glucose Concentration (g/L) |
|---|---|---|---|
| 1 | Day 1 | 0.12 | 4.02 |
|   | Day 2 | 0.59 | 0.20 |
|   | Day 3 | 0.62 | 0.12 |
| 2 | Day 4 | 1.17 | 4.24 |
|   | Day 5 | 2.19 | 0.80 |
|   | Day 6 | 2.62 | 0.36 |
| 3 | Day 7 | 4.39 | 3.31 |
|   | Day 8 | 5.83 | 1.59 |
|   | Day 9 | 5.88 | 1.65 |

As a result, an increase in the alcohol concentration was observed; the alcohol concentration on Day 1 was 0.12% and increased to as high has 5.88% on the last day (Day 9) of the third stage feeding (see Table 20 and FIG. 20). The glucose concentration was observed to decrease on every third day, but in the third stage feeding, the reduction in the concentration was less than in the other two feedings, with about 1.6% of glucose remaining.

Since those brewed in (5-2) to (5-4) had a high alcohol content, they were subjected to distillation on the last day of the stage feedings. The results are shown in Table 21 and FIG. 21.

TABLE 21

List Comparing Alcohol Concentration of Distillate Fractions for Bamboo Shochu Liquor with Rice Koji Fungus Fed Thereto

| Distillate Fractions | 3-2 Alcohol Concentration, Rice Koji Fungus Uniformly Fed (%) | 3-3 Alcohol Concentration, Rice Koji Fungus Decrementally Fed (%) | 3-4 Alcohol Concentration, Rice Koji Fungus Incrementally Fed (%) |
|---|---|---|---|
| Distillate 1 (to 40 ml) | 79.76 | 22.81 | 46.35 |
| Distillate 2 (to 80 ml) | 46.73 | 11.07 | 39.75 |
| Distillate 3 (to 120 ml) | 20.28 | 3.97 | 7.11 |
| Distillate 4 (to 160 ml) | 5.60 | 1.22 | 1.75 |

Figure 21:
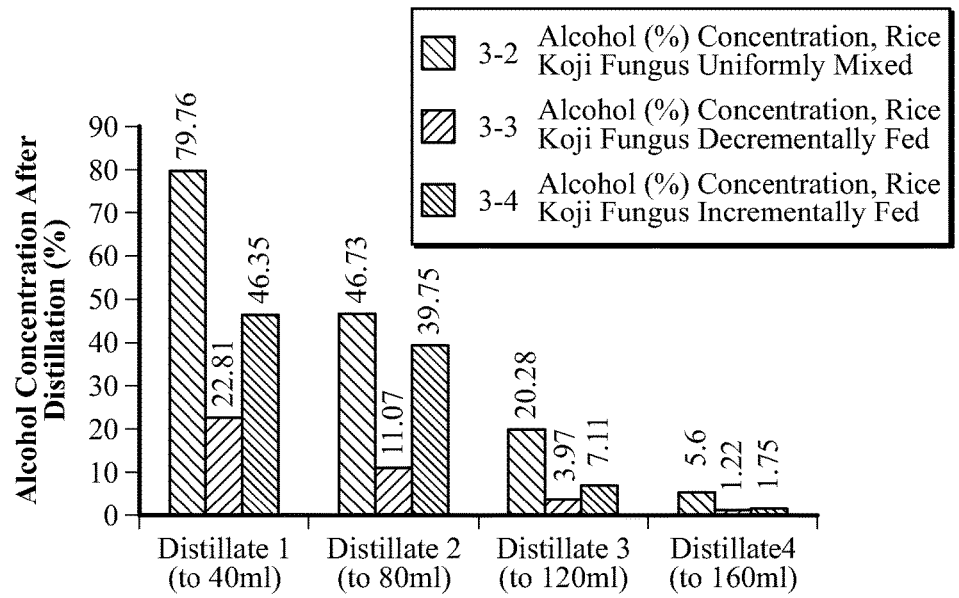
FIG. 21 is a graph showing the alcohol concentration of the distillate fractions of the alcohol obtained according to the method of the present invention.

As a result, the alcohol concentration was highest with the brew obtained by uniformly adding the rice koji fungus, next with that from the step-by-step incremental addition of the rice koji fungus, and lowest with that from the step-by-step decremental addition of the rice koji fungus (see Table 21 and FIG. 21).

(6) Study of Large Volume Alcoholic Fermentation

Figure 22:
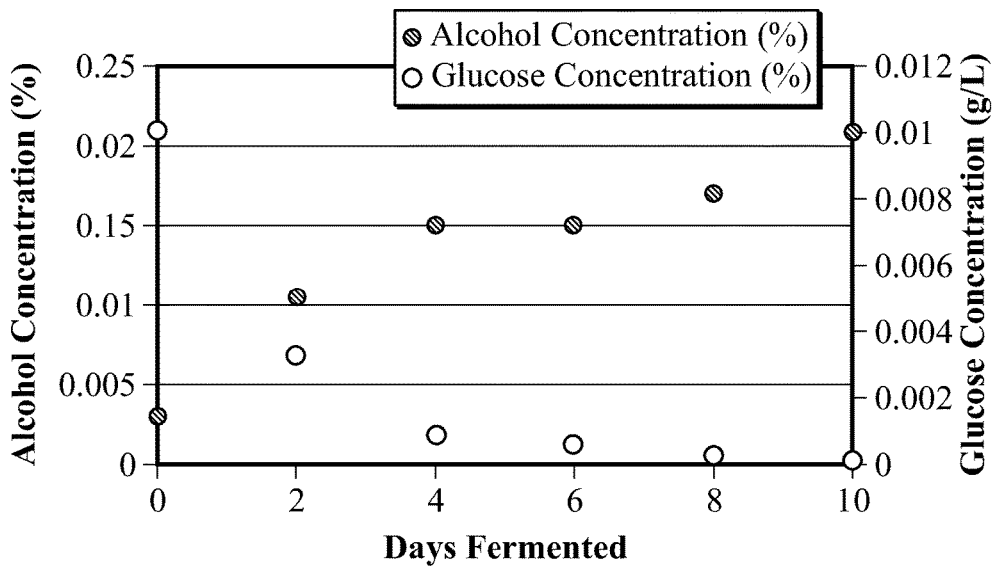
FIG. 22 is a graph showing the alcohol concentration and the glucose concentration as a result of a large volume alcoholic fermentation carried out according to the method of the present invention in one embodiment of the present invention.

Table 22 and FIG. 22 show the measured values of the alcohol and glucose concentrations resulting from scaled-up, large volume alcoholic fermentation.

TABLE 22

Results of Large Volume Alcoholic Fermentation

| | Glucose Concentration (g/L) | Alcohol Concentration (%) |
|---|---|---|
| Day 0 | 0.0101 | 0.003 |
| Day 1 | 0.0033 | 0.011 |
| Day 2 | 0.0009 | 0.015 |
| Day 3 | 0.0006 | 0.015 |
| Day 4 | 0.0004 | 0.017 |
| Day 5 | 0.0003 | 0.021 |

As a result, the alcohol concentration increased with every measurement and was 0.02% on Day 5 at the end of the secondary fermentation. Further, the glucose concentration fell with every measurement and was 0.0003 (g/L) on Day 5 at the end of the secondary fermentation (See Table 22 and FIG. 22).

Example 9

Alcoholic Fermentation Using the MRE-Treated Sugi Cedar and Hinoki Cypress

Growth test of koji fungus used in the primary fermentation and alcoholic fermentation study Experimental materials are as follows. Details of the strains used are shown in Table 23.

MRE enzyme treated sugi cedar, hinoki cypress powder (1 mm mesh sieve)

Mineral water ("Morinomizudayori" Sold by Coca Cola)

Strains: 7 strains

Dry yeast (Product of Nissin Foods Co., Ltd., Nissin Super Cameria)

TABLE 23

Strains Used

| Aspergillus amazake | NBRC30104 | White Koji Fungus |
| Aspergillus orgzae | | |
| Aspergillus cellulosae | NBRC4040 | Yellow Koji Fungus |
| Aspergillus cellulosae | IFO4297 | |
| Aspergillus usami | NBRC4033 | Black Koji Fungus |
| Aspergillus awamori | NBRC4388 | |

Experimental Method (1-1) Mycelial Growth Test by Koji Fungus Type

Mineral water was added to the MRE-treated sugi cedar or hinoki cypress powder to form a 100% hydrated mixture, with 20 g each thereof equally distributed into Petri dishes. Thereafter the mixtures were autoclaved (121° C., 15 min) for a heat treatment and cooled, followed by inoculating with a total of 6 strains, respectively: two white koji fungi types (*Aspergillus amazake* and *Aspergillus orgzae* NBRC 30104); two yellow koji fungi types (*Aspergillus cellulosae* NBRC4040, and IFO4297), and two black koji fungi types (*Aspergillus usami* NBRC4033 and *Aspergillus awamori* NBRC4388), leaving them to grow at 25° C. for 10 days, and studying their mycelial growth. In addition the % hydration was set at 100, from the experimental results on bamboo. See FIG. 3a for the experimental method.

(1-2) Alcoholic Fermentation Using the Koji Fungus or Fungi that Gave Good Results in the Mycelial Growth Test.

Figure 23:
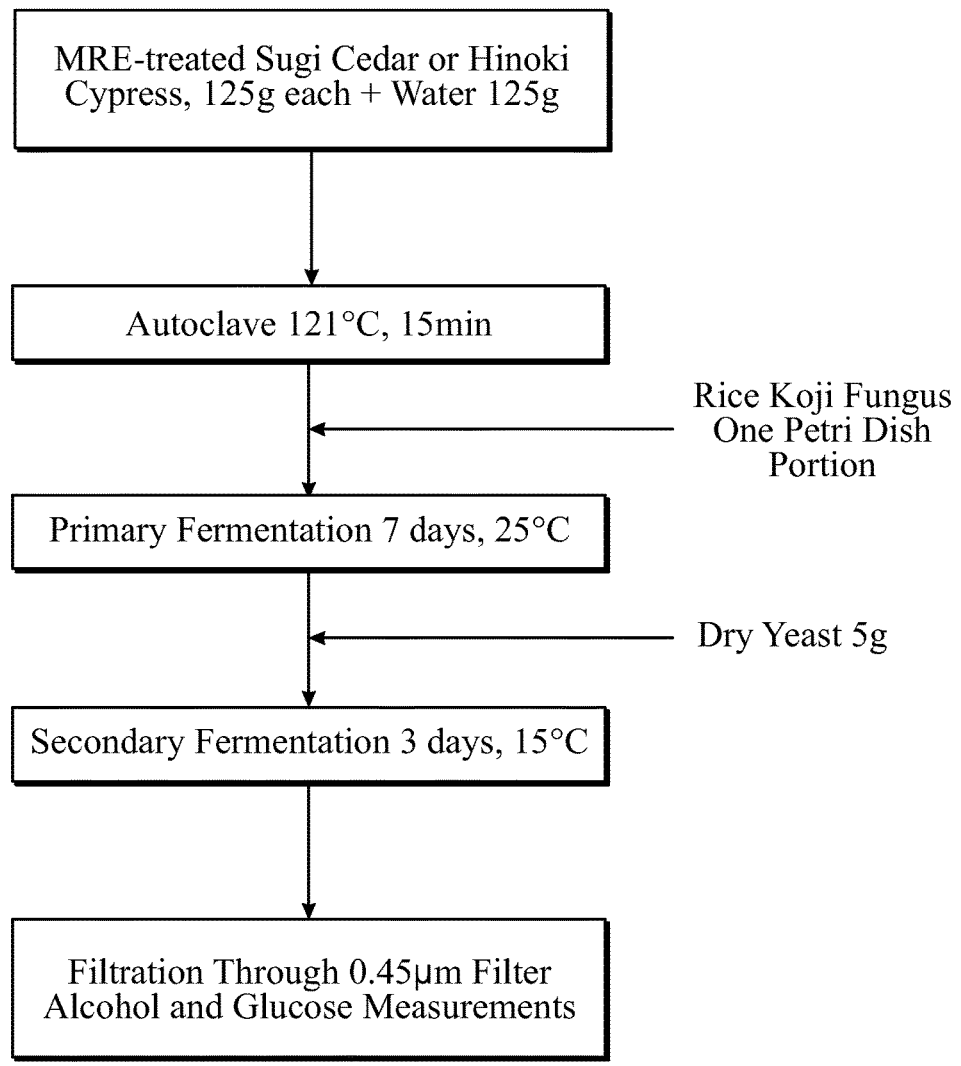
FIG. 23 is an alcoholic fermentation flow sheet using the MRE-treated sugi cedar or hinoki cypress in one embodiment of the present invention.

125 g of the MRE-treated sugi cedar and hinoki cypress, respectively was weighed in and 125 g of mineral water was added thereto, and the mixture was stirred well to achieve 100% hydration. Thereafter, the mixture was autoclaved (121° C., 15 min), cooled, and allowed to ferment as a primary fermentation at 25° C. for 7 days. For a secondary fermentation, dry yeast (Product of Nissin Foods Co., Ltd., Nissin Super Cameria) and 800 g of feed water were added thereto and mixed well, and the mixture was added to the first fermentation mixture, followed by mixing well for performing a secondary fermentation. The secondary fermentation was performed under conditions of 15° C. for 3 days. The fermentation supernatant was fractionated and filtered with a filter; and the alcohol and glucose concentrations were measured. The flow sheet of FIG. 23 shows the operating method.

Example 10

Study of Yeast Suitable for Alcoholic Fermentation

Experimental materials are as follows. In addition, the details of the yeast used are as shown in Table 3.

MRE enzyme treated sugi cedar and hinoki cypress powders (1 mm mesh sieve).

Mineral water ("Morinomizudayori" Sold by Coca Cola).

Strains Used:

Strain for the primary fermentation; *Aspergillus awamori* NBRC438.8

Yeasts used: 7 yeast types for alcoholic fermentability study.

Further, the media used, kit used, conditions for measurement by gas chromatography (GC), conditions for measurement by high-speed liquid chromatography (HPLC), and the like are the same as those used in the experiments with bamboo.

Experimental Method

Figure 24:
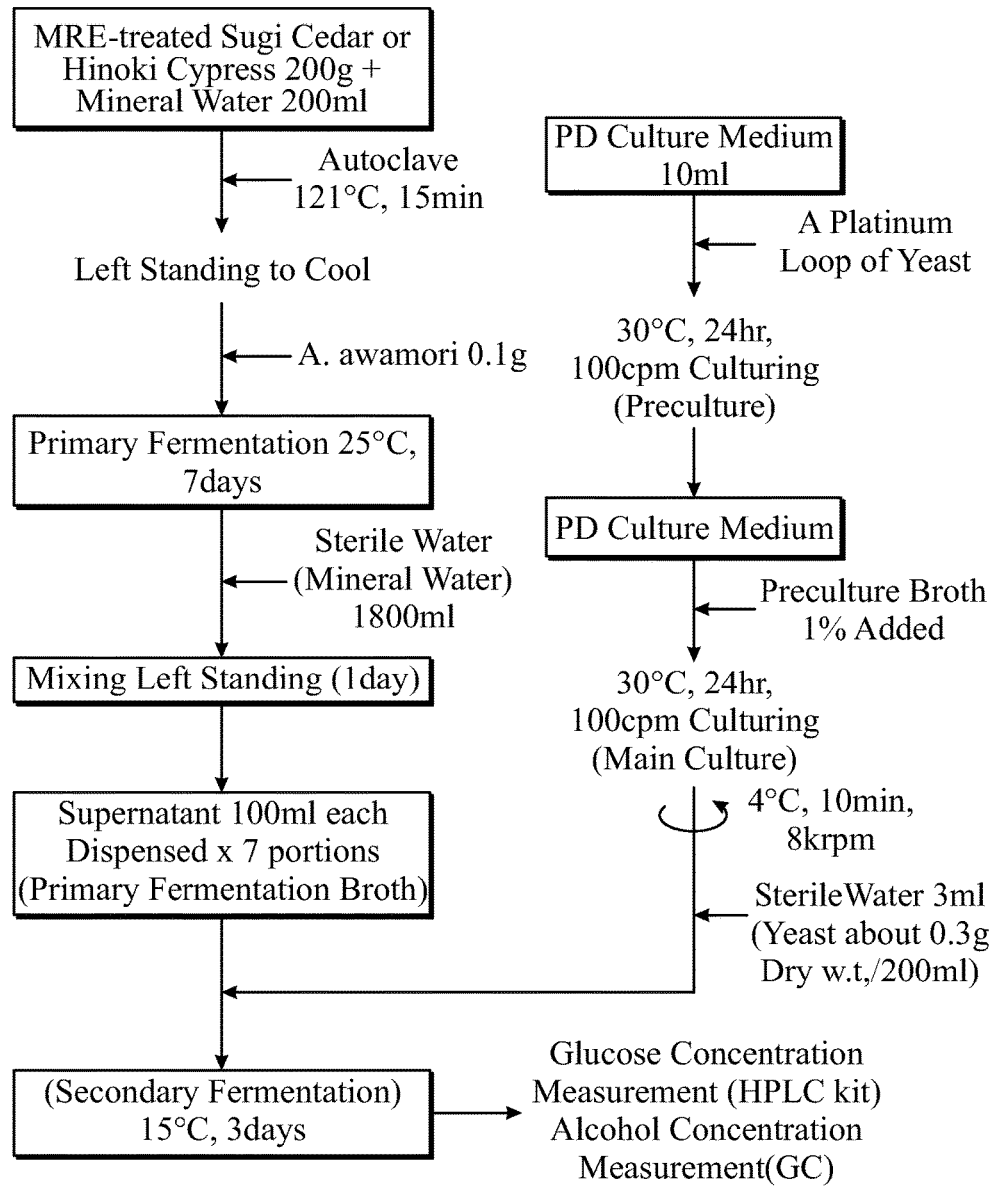
FIG. 24 is a flow sheet for studying the alcoholic fermentability, by yeast, in one embodiment of the present invention.

Procedures for experimental method are shown in FIG. 24.

200 g of the MRE-treated sugi cedar and hinoki cypress, respectively, to which was added mineral water to make them 100% by weight hydrated, was well mixed and autoclaved at 121° C. for 15 min. After the mixture was cooled to room temperature, about 0.1 g of *Aspergillus awamori* was added as a seed koji fungus thereto, followed by mixing well to carry out standing fermentation at 25° C. for 7 days with a gentle stirring every 24 hrs. This was designated a primary fermentation. The primary fermentation product, to which was added 1800 ml of feed water, was well mixed and left standing for 24 hrs. After 24 hrs, the supernatant of the fermentation broth was dispensed 100 ml each into tall 300 ml volume tall beakers. 18φ test tubes holding 10 ml of a PD culture medium were respectively inoculated with a platinum loop of one of the above mentioned yeasts and incubated at 30° C. and 100 cpm for 24 hrs. This was designated a pre-culture; 1% of the pre-culture medium was respectively inoculated into a 500 ml volume Erlenmeyer flask (working volume with 200 ml PD medium) and was incubated at 30° C. and 100 cpm for 24 hrs. This was designated a main culture. After 24 hrs, 200 ml of the main culture was centrifuged using a small size refrigerated centrifuge (TOMY Co., Ltd.) at 4° C. and 8 krpm for 10 minutes to obtain a cultured yeast. The total amount of the cultured yeast was suspended in 3 ml of sterile water and thereafter added to the primary fermentation broth, thereby starting a secondary fermentation. The secondary fermentation was conducted at 15° C. for 3 days under standing condition, with a gentle stirring every 24 hours. During the secondary fermentation the alcohol concentration was measured every 24 hrs with a GC (made by GL Sciences Inc.) and the glucose concentration was measured with the glucose kit. A comparison was made using, as a control, the primary fermentation broth to which yeast was not added.

Example 11

Study of Alcoholic Fermentation with a Stage Feeding
Experimental materials are as follows.
MRE enzyme treated sugi cedar and hinoki cypress powder (1 mm mesh sieve)
Mineral water ("Morinomizudayori" Sold by Coca Cola)
Strains Used:
Strain for the primary fermentation; *Aspergillus awamori* NBRC4388
Yeasts used: 7 yeast types for alcoholic fermentability study
Experimental Method
150 g of water (mineral water) was added to each of 150 g of MRE-treated sugi cedar and hinoki cypress in a stainless-steel kettle, and mixed well. This was followed by autoclaving at 121° C. for 15 min, cooling to room temperature, then adding about 0.1 g of *Aspergillus awamori* NBRC4388 and stirring well so as to uniformly mix the fungus. This mixture was left standing at 25° C. for 3 days. It was gently stirred once a day and was designated a primary fermentation feedstock upon confirming that the mycelia have grown sufficiently over the entire mixture. Then, 500 g of feed water and 0.6 g of yeast (sugi cedar Sacharromyces celevisiae NBRC0244; hinoki cypress: dry yeast), respectively were added, and the mixture was thoroughly mixed. The mixture was left standing at 15° C. for 1 day followed by adding 1200 g of feed water, mixing well and standing at 15° C. for 3 days, and then only the fermentation broth was taken out. 150 g of the primary fermentation feedstock was added to the fermentation broth as a second stage feeding, followed by standing at 15° C. for 3 days. Once again, only the fermentation broth was taken out and 150 g of the primary fermentation feedstock was added thereto as a third stage feeding, followed by standing at 15° C. for 3 days. During the time, the mixture was gently stirred every day, and a visual observation of the state of the fermentation and measurement of the alcohol concentration were performed. The measurement of the alcohol concentration was made with gas chromatography. In addition, with respect to the stage feeding, as it was thought that the presence, if any, of sugi cedar or hinoki cypress powder solid components might possibly inhibit the alcoholic fermentation, a secondary fermentation, the method adopted calls for taking out only the broth after the primary fermentation, thereby carrying out the secondary fermentation.

Figure 25:
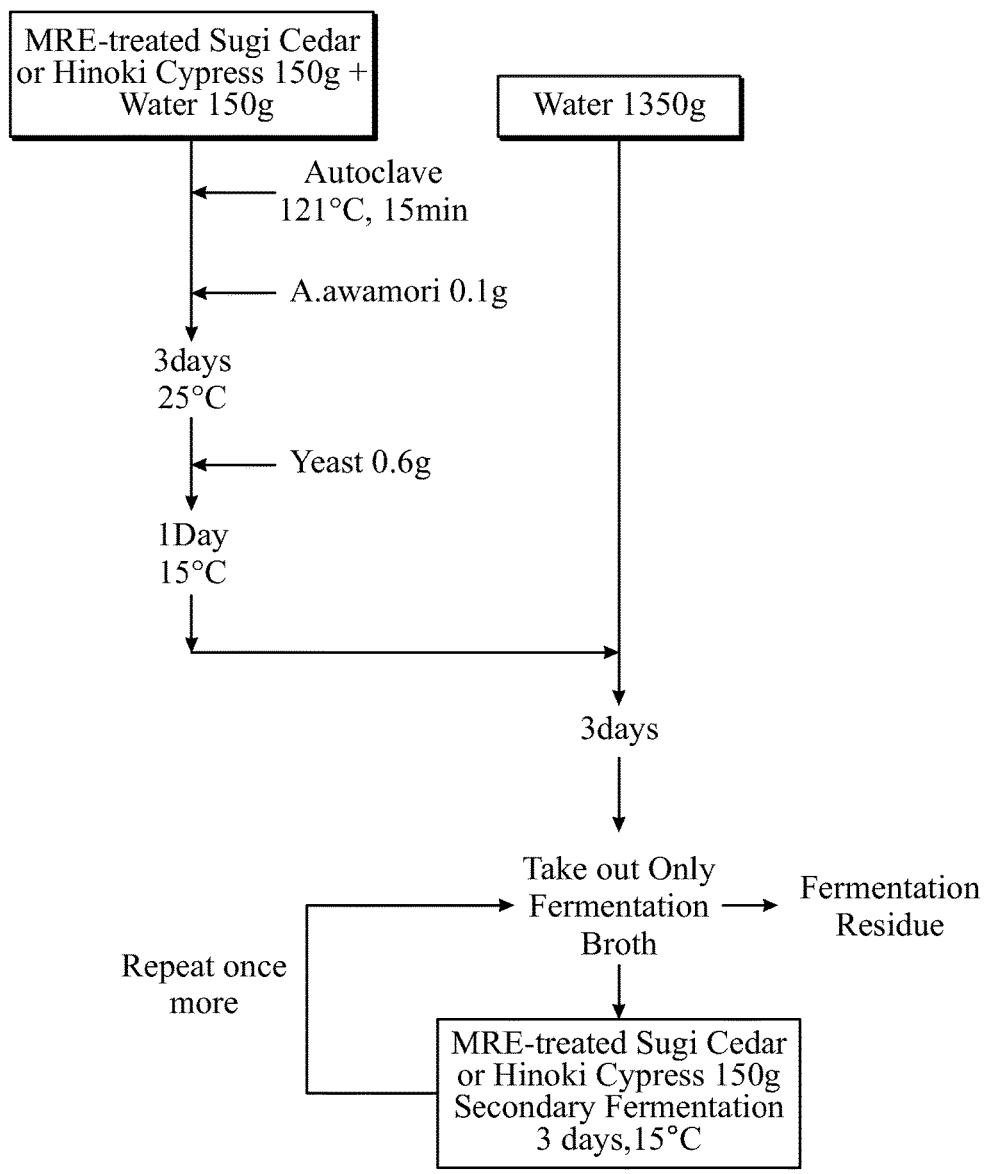
FIG. 25 is a flow sheet for stage feeding of the MRE-treated sugi cedar or hinoki cypress in one embodiment of the present invention.

FIG. 25 shows the flow sheet and Table 24 the fed.\materials.

TABLE 24

List of Fed Materials

|  | First Stage Feeding | Second Stage Feeding | Third Stage Feeding |
| --- | --- | --- | --- |
| MRE-treated Sugi Cedar or Hinoki Cypress | 150 g | 150 g | 150 g |
| Rice Koji Fungus | — | — | — |
| Feed Water | 2000 g | 0 g | 0 g |

Results

Figure 26:
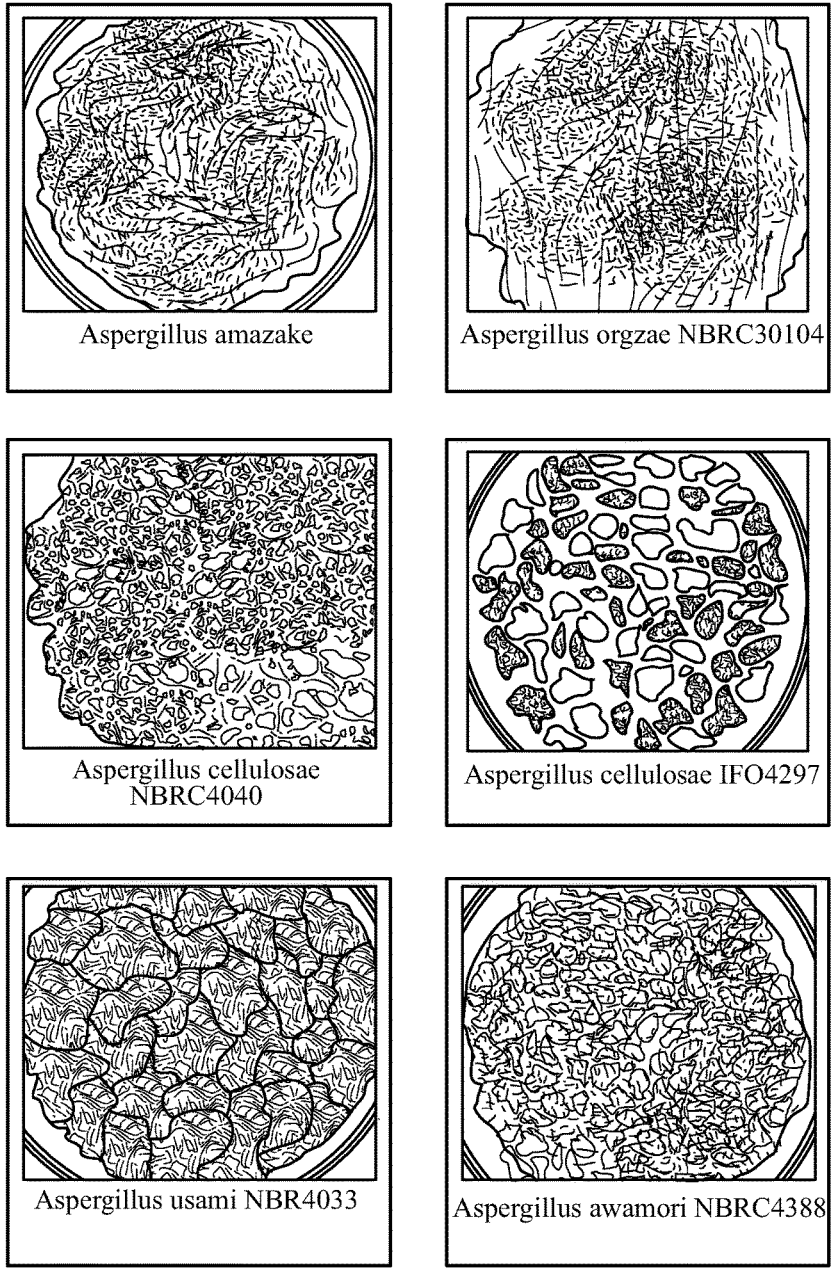
FIG. 26 is Day 10 photographs of a mycelial growth test, by koji fungus type using the MRE-treated sugi cedar in one embodiment of the present invention.

Growth test for koji fungi used in the primary fermentation and study of alcoholic fermentation Table 25 shows the results of the mycelial growth test, by koji fungus type using the MRE-treated sugi cedar; FIG. 26 Day 10 photographs.

TABLE 25

Results of Mycelial Growth Test Using Sugi Cedar

|  | Day 3 | Day 5 | Day 7 | Day 10 |
| --- | --- | --- | --- | --- |
| *Aspergillus amazake* | Δ Only around Part of the Powder | Δ Only around Part of the Powder | ○ The fungus body spread in half of Petri dish | ○ The fungus body spread in 90% of Petri dish |
| *Aspergillus orgzae* NBRC30104 | Δ Only around Part of the Powder | ○ Spread entirely over sugi cedar surface | ⊚ The fungus body spread entirely in Petri dish | ⊚ The fungus body spread entirely in Petri dish |
| *Aspergillus cellulosae* NBRC4040 | X | X | X | Δ Only around Part of the Powder |
| *Aspergillus cellulosae* IFO4297 | ○ Spread entirely over MRE-treated sugi cedar | ⊚ The fungus body spread entirely in Petri dish | ⊚ The fungus body spread entirely in Petri dish | ⊚ The fungus body spread entirely in Petri dish |
| *Aspergillus usami* NBRC4033 | Δ Only around Part of the Powder | ○ Spread entirely over sugi cedar surface | ○ Spread entirely over sugi cedar surface | ⊚ The fungus body spread entirely in Petri dish |
| *Aspergillus awamori* NBRC4388 | ○ Spread entirely over MRE-treated sugi cedar | ⊚ The fungus body spread entirely in Petri dish | ⊚ The fungus body spread entirely in Petri dish | ⊚ The fungus body spread entirely in Petri dish |

Figure 27:
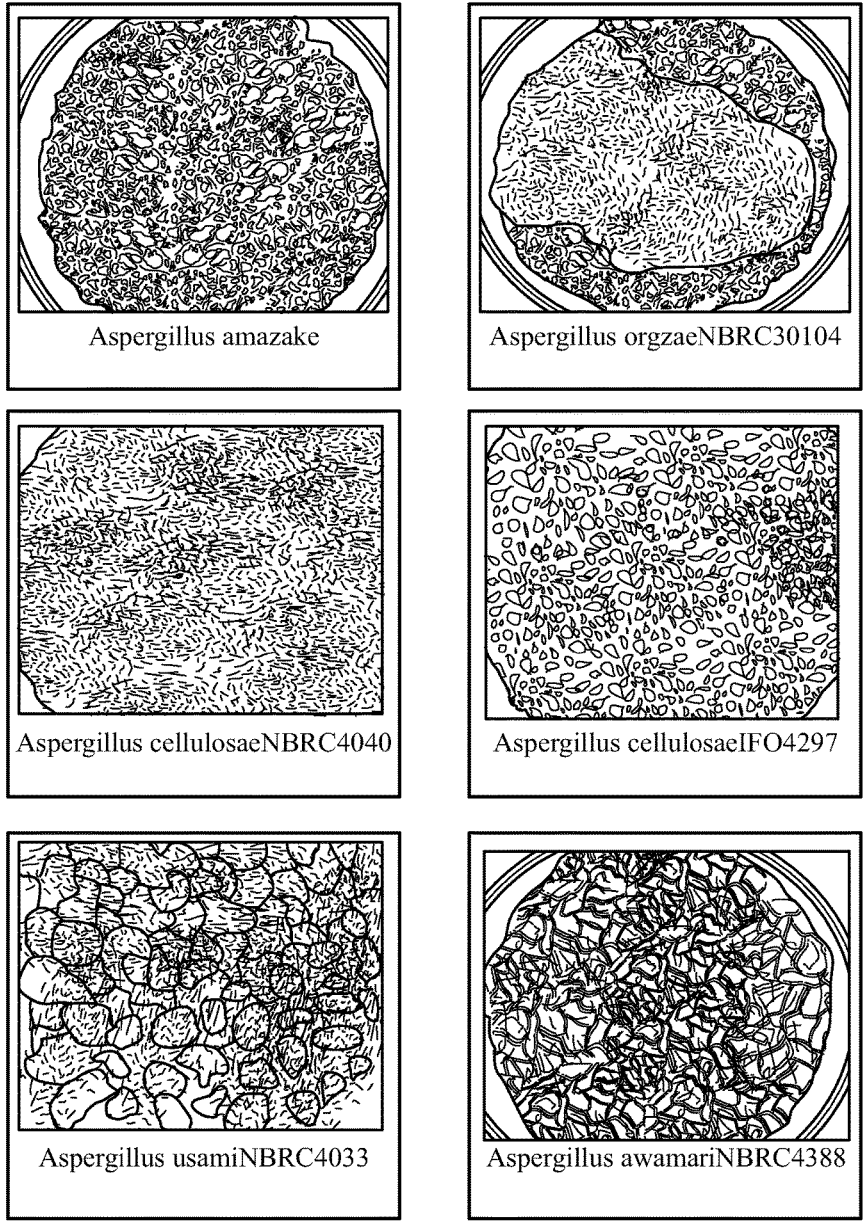
FIG. 27 is Day 10 photographs of a mycelial growth test, by koji fungus type using the MRE-treated hinoki cypress in one embodiment of the present invention.

In addition, Table 26 shows the results of the mycelial growth test, by koji fungus type using the MRE-treated hinoki cypress: FIG. 27 Day 10 photographs.

TABLE 26

Results of Mycelial Growth Test Using HinokiCypress

| | Day 3 | Day 5 | Day 7 | Day 10 |
|---|---|---|---|---|
| *Aspergillus amazake* | X | Δ Only around Part of the Powder | ○ The fungus body spread in 40% of Petri dish | ○ The fungus body spread in 90% of Petri dish |
| *Aspergillus orgzae* NBRC30104 | X | Δ Only around Part of the Powder | Δ Only around Part of the Powder | ○ The fungus body spread in 70% of Petri dish |
| *Aspergillus cellulosae* NBRC4040 | X | X | X | Δ Only around Part of the Powder |
| *Aspergillus cellulosae* IFO4297 | X | X | X | Δ Only around Part of the Powder |
| *Aspergillus usami* NBRC4033 | X | Δ Only around Part of the Powder | ○ Spread entirely over MRE-treated sugi cedar | ◉ The fungus body spread entirely in Petri dish |
| *Aspergillus awamori* NBRC4388 | ◉ The fungus body spread entirely in Petri dish | ◉ The fungus body spread entirely in Petri dish | ◉ The fungus body spread entirely in Petri dish | ◉ The fungus body spread entirely in Petri dish |

For both MRE-treated sugi cedar and hinoki cypress, *Aspergillus awamori* NBRC4388 was the best in mycelial growth with the mycelia spreading over the entire powder thereof at a stage as early as Day 3 (see Tables 25 and 26). In addition, the results showed that it was possible to confirm, for the MRE-treated sugi cedar, also good mycelial growth with 5 fungus strain types, except for *Aspergillus cellulosae* NBRC4040; however the MRE-treated hinoki cypress showed a slower mycelial growth compared to the MRE-treated sugi cedar, with a strain other than the *Aspergillus awamori* NBRC4388.

Table 27 shows the results of performing alcoholic fermentation using for the saccharification in the primary fermentation *Aspergillus awamori* NBRC4388, which gave good results in the mycelial growth tests for the MRE-treated sugi cedar and hinoki cypress.

TABLE 27

Alcoholic Fermentation Using MRE-treated Sugi Cedar as Feedstock

| | Alcohol Concentration (%) | Glucose Concentration (g/L) |
|---|---|---|
| Day 1 | 0.03 | 1.01 |
| Day 2 | 0.04 | 1.04 |
| Day 3 | 0.05 | 1.04 |

TABLE 27-continued

Alcoholic Fermentation Using MRE-treated Hinoki Cypress as Feedstock

| | Alcohol Concentration (%) | Glucose Concentration (g/L) |
|---|---|---|
| Day 1 | 0.01 | 1.20 |
| Day 2 | 0.02 | 1.26 |
| Day 3 | 0.02 | 1.31 |

The alcohol concentration was 0.05% with the MRE-treated sugi cedar and 0.02% with the MRE-treated hinoki cypress (see Table 27). Also, even on Day 3 in the alcoholic fermentation, the glucose concentration remained at not less than 1% in the fermentation broth, an incomplete assimilation for both the MRE-treated sugi cedar and hinoki cypress.

Study of the Yeasts Suitable for Alcoholic Fermentation

Figure 28:
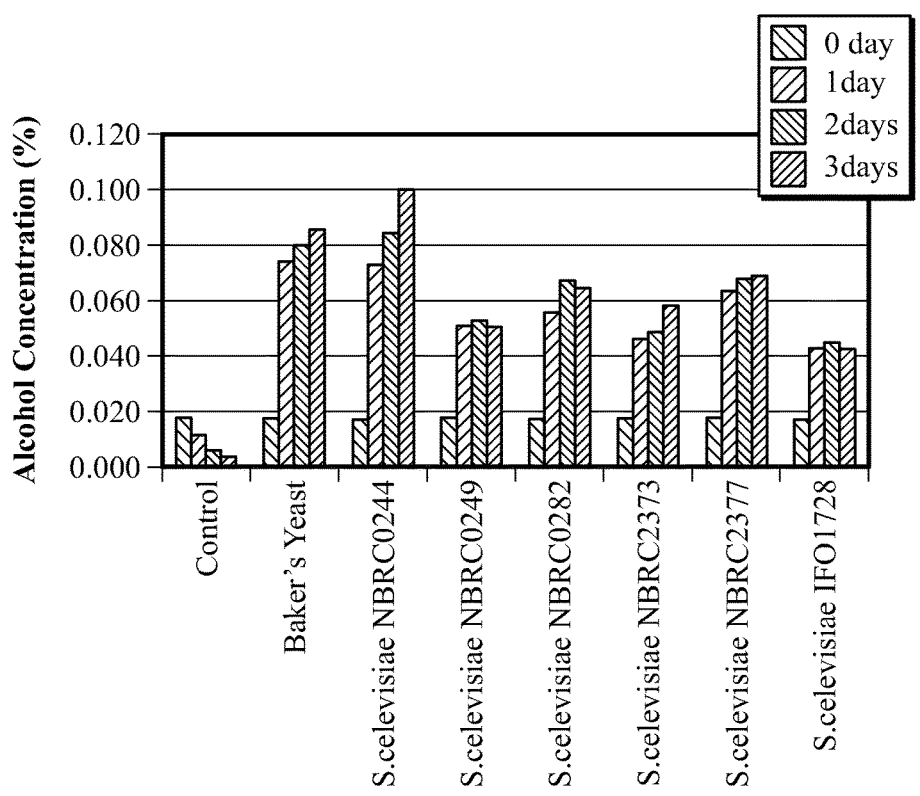
FIG. 28 is a graph showing the alcoholic fermentability, by yeast, using the MRE-treated sugi cedar in one embodiment of the present invention.
Figure 29:
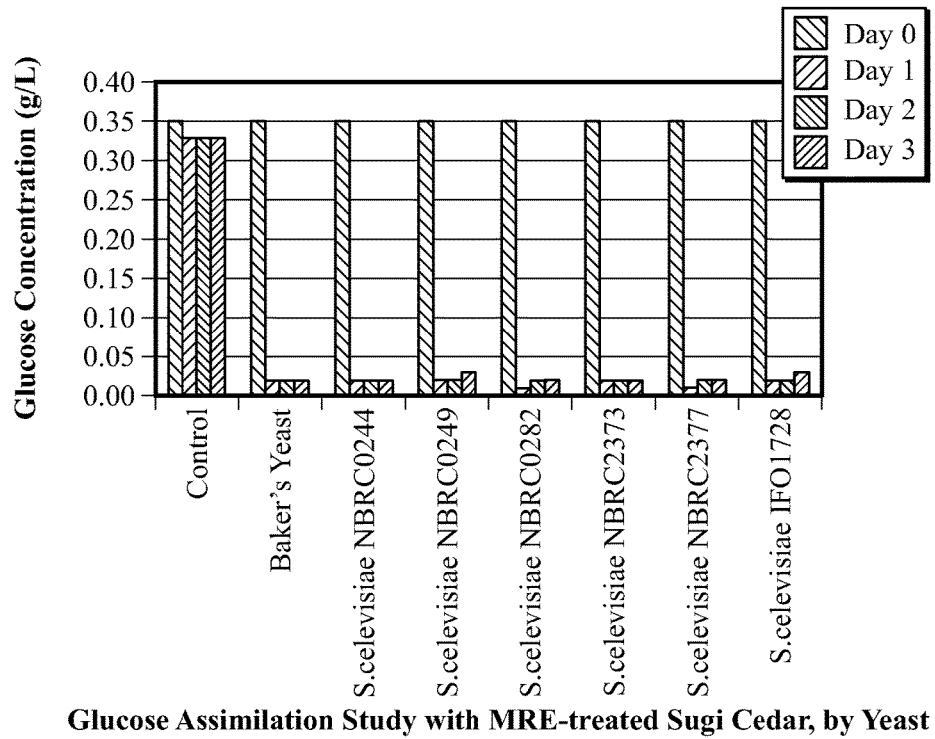
FIG. 29 is a graph showing the glucose concentration in the case of using the MRE-treated sugi cedar in one embodiment of the present invention.

Table 28 and FIG. 28 show the results, by yeast, of the alcoholic fermentability study using the MRE-treated sugi cedar, and Table 29 and FIG. 29 the glucose concentration.

TABLE 28

Alcoholic Fermentability Study Results with MRE-treated Sugi Cedar, by Yeast (Unit %)

| | Control | Baker's Yeast | *S. celevisiae* NBRC0244 | *S. celevisiae* NBRC0249 | *S. celevisiae* NBRC0282 | *S. celevisiae* NBRC2373 | *S. celevisiae* NBRC2377 | *S. celevisiae* IFO1728 |
|---|---|---|---|---|---|---|---|---|
| Day 0 | 0.018 | 0.018 | 0.018 | 0.018 | 0.018 | 0.018 | 0.018 | 0.018 |
| Day 1 | 0.012 | 0.074 | 0.073 | 0.051 | 0.055 | 0.046 | 0.063 | 0.043 |
| Day 2 | 0.006 | 0.080 | 0.084 | 0.052 | 0.067 | 0.049 | 0.068 | 0.045 |
| Day 3 | 0.004 | 0.086 | 0.100 | 0.051 | 0.064 | 0.059 | 0.069 | 0.043 |
| Notes | Strong sugi cedar flavor | Strong sugi cedar flavor | Strong sugi cedar flavor | Strong sugi cedar flavor | Strong sugi cedar flavor | Strong sugi cedar flavor | Strong sugi cedar flavor | Strong sugi cedar flavor |

TABLE 29

Glucose Concentration Measurement Results with MRE-treated Sugi Cedar, by Yeast (Unit g/L)

|  | Control | Baker's Yeast | S. celevisiae NBRC0244 | S. celevisiae NBRC0249 | S. celevisiae NBRC0282 | S. celevisiae NBRC2373 | S. celevisiae NBRC2377 | S. celevisiae IFO1728 |
|---|---|---|---|---|---|---|---|---|
| Day 0 | 0.35 | 0.35 | 0.35 | 0.35 | 0.35 | 0.35 | 0.35 | 0.35 |
| Day 1 | 0.33 | 0.02 | 0.02 | 0.02 | 0.01 | 0.02 | 0.01 | 0.02 |
| Day 2 | 0.33 | 0.02 | 0.02 | 0.02 | 0.02 | 0.02 | 0.02 | 0.02 |
| Day 3 | 0.33 | 0.02 | 0.02 | 0.03 | 0.02 | 0.02 | 0.02 | 0.03 |

Figure 30:
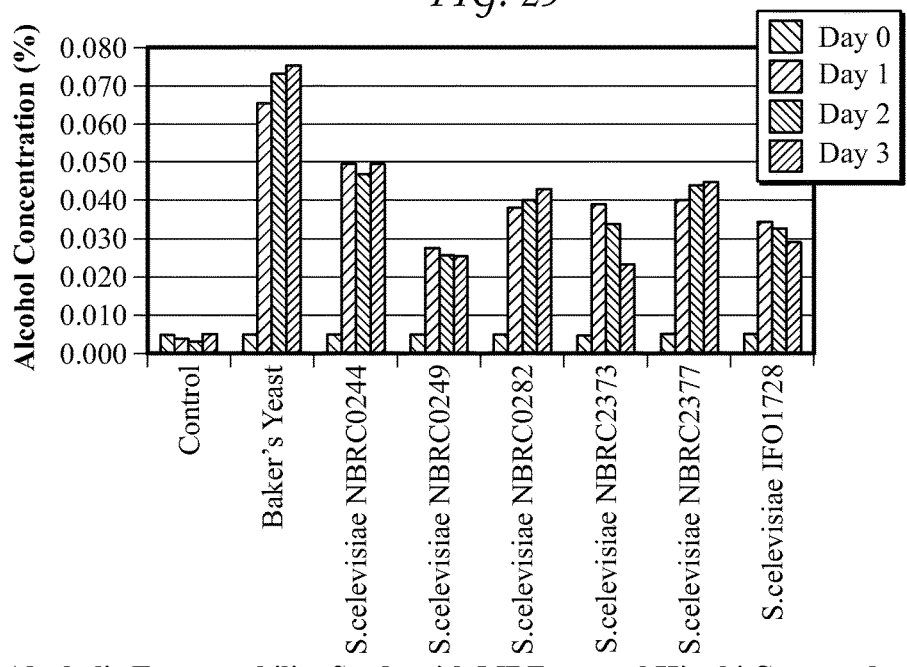
FIG. 30 is a graph showing the alcoholic fermentability, by yeast, using the MRE-treated hinoki cypress in one embodiment of the present invention.
Figure 31:
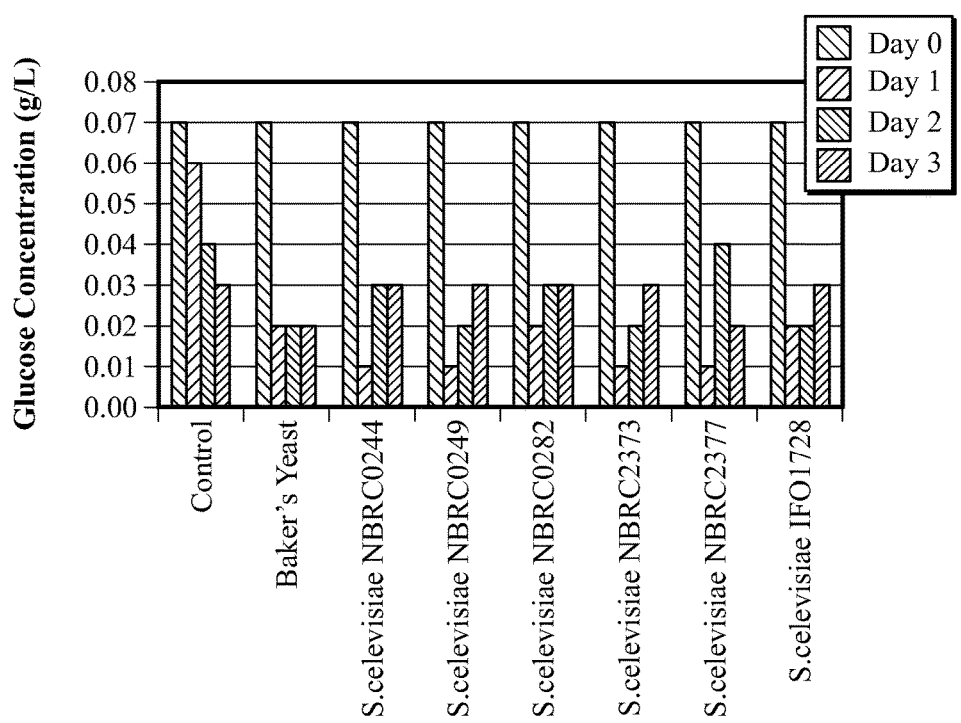
FIG. 31 is a graph showing the glucose concentration in the case of using the MRE-treated hinoki cypress in one embodiment of the present invention.

Table 30 and FIG. 30 show the results, by yeast, of the alcoholic fermentability study with the MRE-treated hinoki cypress; and Table 31 and FIG. 31 the glucose concentration.

TABLE 30

Alcoholic Fermentability Study Results with MRE-treated Hinoki Cypress, by Yeast (Unit %)

|  | Control | Baker's Yeast | S. celevisiae NBRC0244 | S. celevisiae NBRC0249 | S. celevisiae NBRC0282 | S. celevisiae NBRC2373 | S. celevisiae NBRC2377 | S. celevisiae IFO1728 |
|---|---|---|---|---|---|---|---|---|
| Day 0 | 0.005 | 0.005 | 0.005 | 0.005 | 0.005 | 0.005 | 0.005 | 0.005 |
| Day 1 | 0.004 | 0.066 | 0.050 | 0.028 | 0.038 | 0.039 | 0.041 | 0.034 |
| Day 2 | 0.003 | 0.074 | 0.047 | 0.026 | 0.040 | 0.034 | 0.044 | 0.033 |
| Day 3 | 0.005 | 0.075 | 0.050 | 0.026 | 0.043 | 0.023 | 0.045 | 0.029 |
| Notes | Strong hinoki cypress flavor | Strong hinoki cypress flavor | Strong hinoki cypress flavor | Strong hinoki cypress flavor | Strong hinoki cypress flavor | Strong hinoki cypress flavor | Strong hinoki cypress flavor | Strong hinoki cypress flavor |

TABLE 31

Glucose Concentration Measurement Results with MRE-treated Hinoki Cypress, by Yeast (Unit g/L)

|  | Control | Baker's Yeast | S. celevisiae NBRC0244 | S. celevisiae NBRC0249 | S. celevisiae NBRC0282 | S. celevisiae NBRC2373 | S. celevisiae NBRC2377 | S. celevisiae IFO1728 |
|---|---|---|---|---|---|---|---|---|
| Day 0 | 0.07 | 0.07 | 0.07 | 0.07 | 0.07 | 0.07 | 0.07 | 0.07 |
| Day 1 | 0.06 | 0.02 | 0.01 | 0.01 | 0.02 | 0.01 | 0.01 | 0.02 |
| Day 2 | 0.04 | 0.02 | 0.03 | 0.02 | 0.03 | 0.02 | 0.04 | 0.02 |
| Day 3 | 0.03 | 0.02 | 0.03 | 0.03 | 0.03 | 0.03 | 0.02 | 0.03 |

As a result of the study of alcoholic fermentability, by yeast, using the MRE-treated sugi cedar, it was *S. celevisiae* NBRC0244 that showed the highest value of the alcohol concentration (see Table 28 and FIG. 28). Further, for the MRE process hinoki cypress used as a feedstock, baker's yeast gave the highest alcohol concentration (see Table 30 and FIG. 30). As to the flavors there remained strong flavors characteristic of sugi cedar and hinoki cypress woods (see Table 30 and Table 28), with essentially no flavor of the yeast sensed.

Study of alcoholic fermentation in a stage feeding of only the MRE-treated sugi cedar or hinoki cypress.

Figure 32:
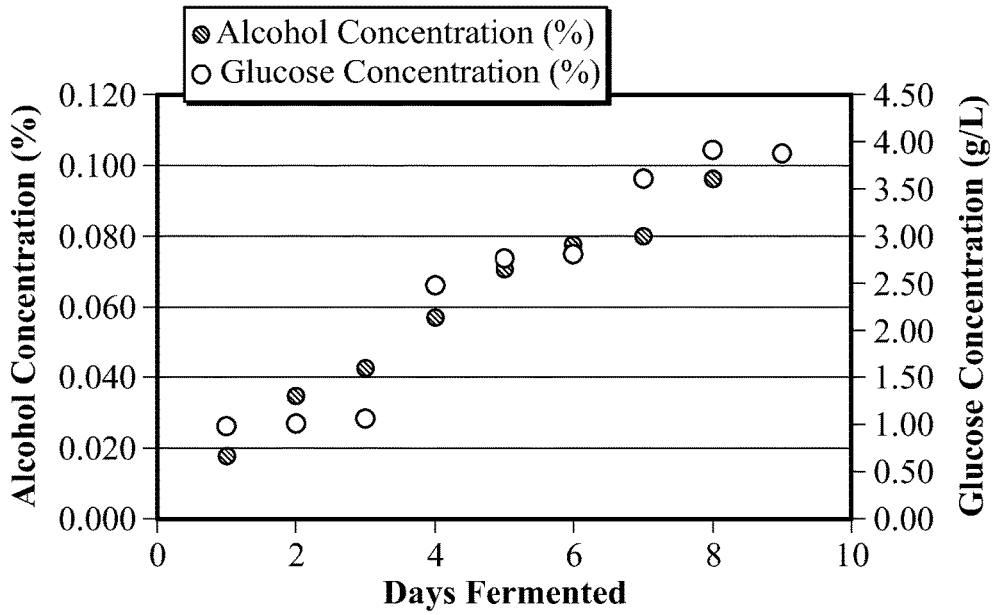
FIG. 32 is a graph showing the alcohol concentration and the glucose concentration in the case of a stepwise feed using the MRE-treated sugi cedar in one embodiment of the present invention.

Table 32 and FIG. 32 show the results or alcohol concentration and the glucose concentration in a stage feeding of only the MRE-treated sugi.

TABLE 32

9 Day Alcoholic Fermentation with Stage Feeding of MRE-treated Sugi Cedar alone And Glucose Concentration (Before Distillation)

| Number of Feedings | Alcoholic Fermentation, Days | Alcohol Concentration (%) | Glucose Concentration (g/L) |
|---|---|---|---|
| 1 | Day 1 | 0.018 | 0.98 |
|  | Day 2 | 0.035 | 1.01 |
|  | Day 3 | 0.043 | 1.06 |
| 2 | Day 4 | 0.057 | 2.48 |
|  | Day 5 | 0.071 | 2.76 |
|  | Day 6 | 0.078 | 2.81 |
| 3 | Day 7 | 0.080 | 3.61 |
|  | Day 8 | 0.096 | 3.91 |
|  | Day 9 | 0.103 | 3.88 |

Figure 33:
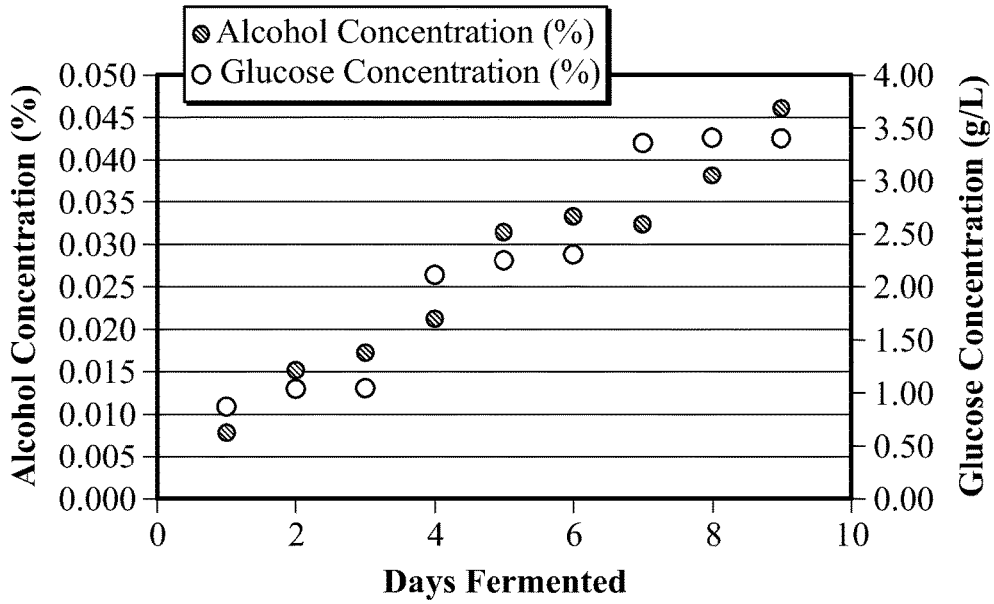
FIG. 33 is a graph showing the alcohol concentration and the glucose concentration in the case of a stepwise feed using the MRE-treated hinoki cypress in one embodiment of the present invention.
Figure 34:
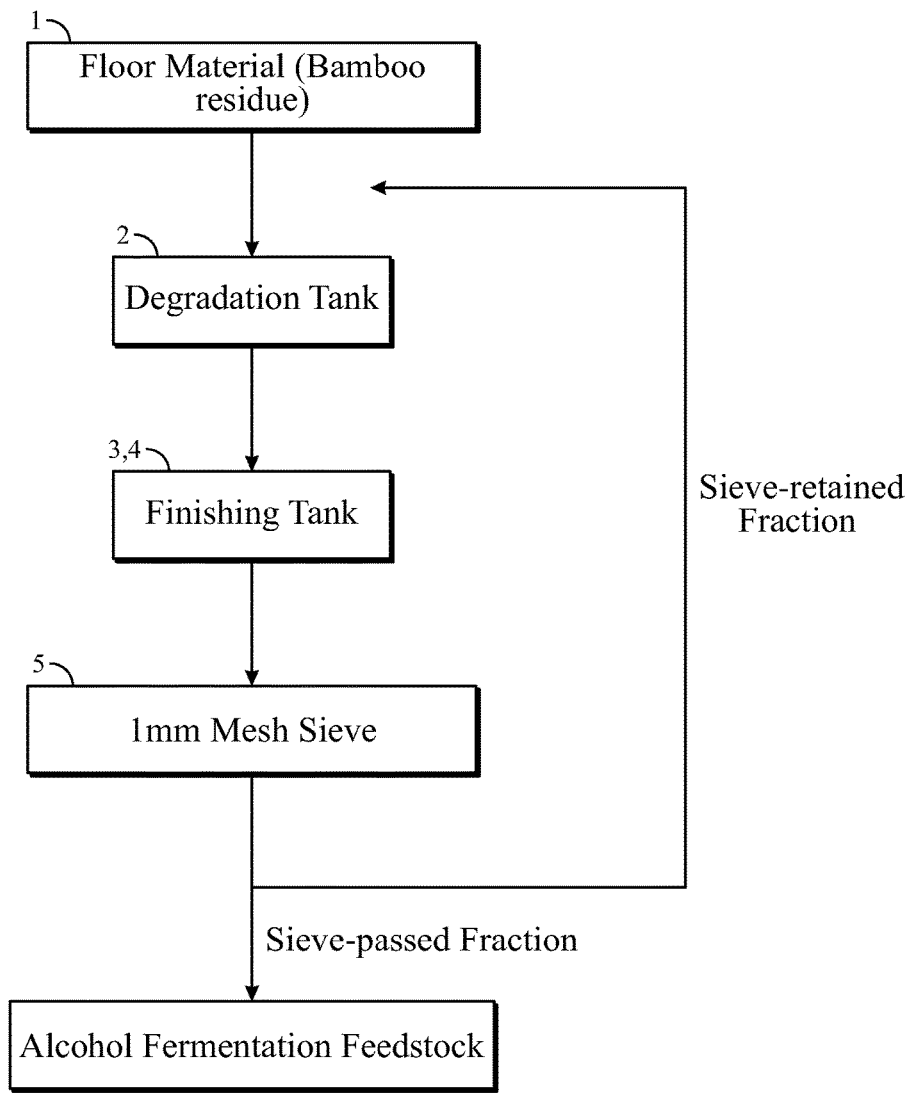
FIG. 34 is a schematic of a method of production of MRE-treated Bamboo.

In addition. Table 33 and FIG. 33 show the results of the alcohol concentration and the glucose concentration in a stage feeding of only the MRE-treated hinoki cypress.

TABLE 33

9 Day Alcoholic Fermentation with Stage Feeding of MRE-treated
Hinoki Cypress alone And
Glucose Concentration (Before Distillation)

| Number of Feedings | Alcoholic Fermentation, Days | Alcohol Concentration (%) | Glucose Concentration (g/L) |
|---|---|---|---|
| 1 | Day 1 | 0.008 | 0.87 |
|   | Day 2 | 0.015 | 1.04 |
|   | Day 3 | 0.017 | 1.05 |
| 2 | Day 4 | 0.021 | 2.12 |
|   | Day 5 | 0.031 | 2.25 |
|   | Day 6 | 0.033 | 2.31 |
| 3 | Day 7 | 0.032 | 3.36 |
|   | Day 8 | 0.038 | 3.41 |
|   | Day 9 | 0.046 | 3.41 |

It was possible to confirm that the alcohol concentration of the MRE-treated sugi cedar and hinoki cypress increased in every measurement (See FIGS. 32 and 33). In addition, the alcohol concentration on Day 9 in the fermentation was 0.103% with the MRE-treated sugi cedar, and 0.046% with the MRE-treated hinoki cypress. However, since the glucose concentration also increased each day with both the sugi cedar and hinoki cypress, it was suggested that the glucose has not been fully assimilated.

It addition, it is needless to state that the present invention can be modified in various ways, and a variety of modifications are enabled within a range of not changing the gist of the present invention without being limited to the one embodiment described above.

What is claimed is:

1. A method for producing alcohol from wood, comprising:
a step of applying mother cell lytic enzymes formed through cytolysis associated with a spore formation of a spore-forming aerobic bacteria to a wood, thereby degrading the wood into a powdery state and obtaining a wood degradation product;
a step of sterilizing the wood degradation product;
a step of applying a koji fungus to the sterilized wood degradation product thereby carrying out a primary fermentation;
a step of adding a yeast to a fermentation broth obtained by the primary fermentation thereby carrying out a secondary fermentation; and
a step of filtering a fermentation broth obtained by the secondary fermentation,
wherein the mother cell lytic enzymes are obtained by incubating the spore-forming aerobic bacteria, placing a resultant culture medium under a starvation condition, thereby causing the bacteria to internally sporulate, and removing from a culture medium impurities containing the internally sporulated bacteria, and
wherein the spore-forming aerobic bacteria is a symbiotic bacteria group consisting of *Bacillus* sp., *Lysinibacillus fusiformis*, *Bacillus sonorensis*, *Lysinibacillus* sp., and *Comamonas* sp.

2. The method as set forth in claim 1, wherein the wood is selected from bamboo, Japanese cedar, and Japanese cypress.

3. The method as set forth in claim 1, wherein the koji fungus is selected from *Aspergillus amazake*, *Aspergillus orgzae* (NBRC30104), *Aspergillus orgzae* (NBRC30113), *Aspergillus cellulosae* (NBRC4040), *Aspergillus cellulosae* (IFO4297), *Aspergillus usami* (NBRC4033), and *Aspergillus awamori* (NBRC4388).

4. The method as set forth in claim 1, wherein the yeast is selected from baker's yeast, *Saccharomyces celevisiae* (NBRC0244), *Saccharomyces celevisiae* (NBRC0249), *Saccharomyces celevisiae* (NBRC0282), *Saccharomyces celevisiae* (NBRC2373), *Saccharomyces celevisiae* (NBRC2377), and *Saccharomyces celevisiae* (IFO1728).

5. The method as set forth in claim 1, wherein the wood is immersed in a degradation solution containing the mother cell lytic enzymes and/or spores formed by spore formation of the spore-forming aerobic bacteria, and is degraded by aerating the solution.

* * * * *